(12) United States Patent
Sadowsky et al.

(10) Patent No.: US 6,369,299 B1
(45) Date of Patent: Apr. 9, 2002

(54) TRANSGENIC PLANTS EXPRESSING BACTERIAL ATRAZINE DEGRADING GENE ATZA

(75) Inventors: Michael J. Sadowsky, Roseville; Lawrence P. Wackett, St. Paul; Carroll P. Vance, New Brighton; Deborah A. Samac, Brooklyn Park, all of MN (US)

(73) Assignees: Regents of the University of Minnesota, Minneapolis, MN (US); Department of Agriculture, Peoria, IL (US)

( * ) Notice: Subject to any disclaimer, the term of this patent is extended or adjusted under 35 U.S.C. 154(b) by 0 days.

(21) Appl. No.: 09/329,535

(22) Filed: Jun. 10, 1999

(51) Int. Cl.[7] ............................. A01H 5/00; A01B 79/02
(52) U.S. Cl. ........................................ 800/298; 47/58.1
(58) Field of Search ................................. 800/298, 300, 800/320, 278; 435/469, 195, 419, 418; 47/58.1

(56) References Cited

U.S. PATENT DOCUMENTS 5,073,677 A * 12/1991 Helmer et al. .............. 800/300
5,508,193 A    4/1996 Mandelbaum et al. ... 435/253.3
6,265,201 B1 *  7/2001 Wackett et al.

FOREIGN PATENT DOCUMENTS

EP    0 218 571     4/1987
WO   WO 97/15675    5/1997
WO   WO 98/31816    7/1998

OTHER PUBLICATIONS

Altschul et al., "Gapped BLAST and PSI–BLAST: a new generation of protein database search programs," *Nucl. Acids Res.*, 25, 3389–3402 (1997).
Austin et al., "Production and field performance of transgenic alfalfa (*Medicago sativa* L.) expressing alpha–amylase and manganese–dependent lignin peroxidas," *Euphytica*, 85, 381–393 (1995).
Baker et al., "Herbicide Resistance," *Tropical Grassy Weeds*, 96–105, CAB International, Wallingford, England (1991).
Bingham, "Registration of Alfalfa Hybrid Regen–Sy Germplasm for Tissue Culture and Transformation Research," *Crop Sci.*, 31, 1098 (1991).
Brown et al., "Role of genetic background in *somatic embryogenesis* in *Medicago*," *Plant Cell Tissue Organ Culture*, 4, 111–122 (1985).
Cook, "Biodegradation of s–triazine xenobiotics," *FEMS Microbiol. Rev.*, 46, 93–116 (1987).
Crossway et al., "Integration of foreign DNA following microinjection of tobacco mesophyll protoplasts," *Mol. Gen. Genet.*, 202, 179–185 (1986).

Daniell et al., "Containment of herbicide resistance through genetic engineering of the chloroplast genome,"*Nature Biotechnol*, 16, 345–348 (1998).
De Souza et al., "Cloning, Characterization, and Expression of a Gene Region from Pseudomonas sp. Strain ADP Involved in the Dechlorination of Atrazine,"*Applied Environ. Microbiol.*, 61, 3373–3378 (1995).
Dellaporta et al., "Molecular Cloning of the Maize R–nj Allele by Transposon Tagging with Ac," *Chromosome Structure and Function*, Plenum Press, New York, 263–282 (1988).
Elhai et al., "Conjugal Transfer of DNA to Cyanobacteria," *Methods Enzymol.*167, 747–754 (1988).
Gallie, "Posttranscriptional Regulation of Gene Expression in Plants," *Annu. Rev. Plant Physiol. Plant Mol. Biol.*, 44, 77–105 (1993).
Gallie et al., "The 5'–leader sequence of tobacco mosaic virus RNA enhances the expression of foreign gene transcripts in vitro and in vivo," *Nucl. Acids Res.*, 15, 3257–3273 (1987).
Gamborg et al., "Nutrient Requirements of Suspension Cultures of Soybean Root Cells," *Experimental Cell Research*, 50, 151–158 (1968).
Heijne et al., "Domain structure of mitochondrial and chloroplast targeting peptides," *Eur. J. Biochem.*, 180, 535–545 (1989).
Ikuta et al., "The α–Amylase Gene as a Marker for Gene Cloning: Direct Screening of Recombinant Clones," *Biotech.*, 8, 241–242 (1990).
Jobling et al., "Enhanced translation of chimaeric messenger RNAs containing a plant viral untranslated leader sequence," *Nature*, 325, 622–625 (1987).
Katz et al., "Cloning and Expression of the Tyrosinase Gene from *Streptomyces antibioticus* in *Streptomyces lividans*," *J. Gen. Microbiol.*, 129, 2703–2714 (1983).
Keegstra et al., "Chloroplastic Precursors and Their Transport Across the Envelope Membranes," *Ann. Rev. Plant Physiol. Plant Mol. Biol.*, 40, 471–501 (1989).
Klein et al., "High–velocity microprojectiles for delivering nucleic acids into living cells," *Nature*, 327, 70–73 (1987).
LeBaron et al., "Summary of Accomplishments, Conclusions, and Future Needs," *Herbicide Resistance in Plants*, 349–362, Wiley, N.Y. (1982).

(List continued on next page.)

Primary Examiner—Amy J. Nelson
Assistant Examiner—David H Kruse
(74) Attorney, Agent, or Firm—Mueting, Raasch & Gebhardt, P.A.

(57) ABSTRACT

The present invention provides plants that dehalogenate at least one s–triazine. The plants can include an exogenous coding region that imparts the ability to degrade at least one s–triazine. The present invention further provides methods for degrading, more preferably detoxifying, at least one s–triazine with an s–triazine degrading plant.

8 Claims, 3 Drawing Sheets

OTHER PUBLICATIONS

LeBaron et al., "Herbicide resistance in weeks and crops," *Managing Resistance to Agrochemicals*, ACS Symposium Ser. 421, ACS Books, Washington, D.C., 336–352 (1990).

LeBaron, "Ways and means to influence the activity and the persistence of triazine herbicides in soils," *Residue Rev.*, 32, 311–353 (1970).

Lee et al., "Superoxide dismutase: An evolutionary puzzle," *Proc. Natl. Acad. Sci. USA*, 82, 824–828 (1985).

Leong et al., "Heme Biosynthesis in Rhizobium," *J. Biol. Chem.*, 257, 8724–8730 (1982).

Mandlebaum et al., "Mineralization of the s–Triazine Ring of Atrazine by Stable Bacterial Mixed Cultures," *Appl. Environ. Microbiol.*, 59, 1695–1701 (1993).

Mets et al., "Prospects for Genetic Modification of Plants for Resistance to Triazine Herbicides," *Biotechnology in Plant Science: Relevance to Agriculture in the Eighties*, pp. 301–312, Academic Press, Florida (1985).

Mullineaux, "Genetically Engineered Plants for Herbicide Resistance," *Plant Genetic Manipulation for Crop Protection*, pp. 75–107, CAB International, Wallingford, England (1992).

Murray et al., "Codon usage in plant genes," *Nucl. Acids Res.*, 17, 477–498 (1989).

Niedz et al., "Green fluorescent protein: an in vivo reporter of plant gene expression," *Plant Cell Reports*, 14, 403–406 (1995).

NIH Guidelines for Research Involving Recombinant DNA Molecules, *Federal Register*, 59, Jul. 5, 1994 (59 FR 34496–34547).

Ooms et al., "Octopine Ti–Plasmid Deletion Mutants of *Agrobacterium tumefaciens* with Emphasis on the Right Side of the T–Region," *Plasmid*, 7, 15–29 (1982).

Oettmeier et al., "Effect of Different Photosystem II Inhibitors on Chloroplasts Isolated from Species Either Susceptible or Resistant Toward s–Triazine Herbicides," *Pesticide Biochem. Physiol.*, 18, 357–367 (1982).

Ow et al., "Transient and Stable Expression of the Firefly Luciferase Gene in Plant Cells and Transgenic Plants," *Science*, 234, 856–859 (1986).

Paszkowski et al., "Direct gene transfer to plants," *EMBO J.*, 3, 2717–2722 (1984).

Prasher et al., "Cloning and Expression of the cDNA Coding for Aequorin, a Bioluminescent Calcium–Binding Protein," *Biochem. Biophys. Res. Comm.*, 126, 1259–1268 (1985).

Przibilla et al., "Site–Specific Mutagenesis of the D1 Subunit of Photosystem II in Wild–Type Chlamydomonas," *Plant Cell.*, 3, 169–174 (1991).

Ryan, "Resistance of Common Groundsel to Simazine and Atrazine," *Weed Sci.*, 18, 614–616 (1970).

Sadowsky et al., "Use of Phytoremediation Strategies to Bioremediate Contaminated Soils and Water," *Biology of Plant–Microbe Interactions*, International Society for Molecular Plant–Microbe Interactions, 527–532 (1996).

Shah et al., "Engineering Herbicide Tolerance in Transgenic Plants," *Science*, 233, 478–481 (1986).

Sikka et al., "Dissipation of Atrazine from Soil by Corn, Sorghum, and Johnsongrass," *Weeds*, 14, 289–293 (1966).

Stemmer et al., "Single–step assembly of a gene and entire plasmid from large numbers of oligodeoxyribonucleotides," *Gene*, 164, 49–53 (1995).

Sutcliffe, "Nucleotide sequence of the ampicillin resistance gene of *Escherichia coli* plasmid pBR322," *Proc. Natl. Acad. Sci. USA*, 75, 3737–3741 (1978).

USDA, "Clean Up Herbicides with Plants," *USDA: Putting Research to Work for America*, 12 (1997).

Widmer et al., "Kinetics of Atrazine Hydrolysis in Water," *J. Environ. Sci. Health*, B28, 19–18 (1993).

Wych et al., "Simultaneous Measurement of Nitrogen Fixation Estimated by Acetylene–Ethylene Assay and Nitrate Absorption by Soybeans," *Plant Physiol.*, 62, 443–448 (1978).

Zukowski et al., "Chromogenic identification of genetic regulatory signals in *Bacillus subtilis* based on expression of a cloned *Pseudomonas gene*," *Proc. Natl. Acad. Sci. USA*, 80, 1101–1105 (1983.

DeSouza et al. Atrazine chlorohydrolase from Pseudomonas sp. strain ADP: gene sequence, enzyme purification and protein characterization. J Bacteriology 1996, 178(16):4894–4900.*

Yuan et al. Modification of plant components. Current Opinion in Biotechnology 1997, 8:227–233, see page 231.*

* cited by examiner

```
                                                                          TT
   3  TTTCGATGGC ATAATATCTG CGTTGCGACG TGTAACACAC TATTGGAGAC ATATCATGCA
  63  AACGCTCAGC ATCCAGCACG GTACCCTCGT CACGATGGAT CAGTACCGCA GAGTCCTTGG
 123  GGATAGCTGG GTTCACGTGC AGGATGGACG GATCGTCGCG CTCGGAGTGC ACGCCGAGTC
 183  GGTGCCTCCG CCAGCGGATC GGGTGATCGA TGCACGCGGC AAGGTCGTGT ACCCGGTTT
 243  CATCAATGCC CACACCCATG TGAACCAGAT CCTCCTGCGC GGAGGGCCCT CGCACGGGCG
 303  TCAATTCTAT GACTGGCTGT TCAACGTTGT GTATCCGGGA CAAAAGGCGA TGAGACCGGA
 363  GGACGTAGCG GTGGCGGTGA GGTTGTATTG TGCGGAAGCT GTGCGCAGCG GGATTACGAC
 423  GATCAACGAA AACGCCGATT CGGCCATCTA CCCAGGCAAC ATCGAGGCCG CGATGGCGGT
 483  CTATGGTGAG GTGGGTGTGA GGGTCGTCTA CGCCCGCATG TTCTTTGATC GGATGGACGG
 543  GCGCATTCAA GGGTATGTGG ACGCCTTGAA GGCTCGCTCT CCCCAAGTCG AACTGTGCTC
 603  GATCATGGAG GAAACGGCTG TGGCCAAAGA TCGGATCACA GCCTGTCAG. ATCAGTATCA
 663  TGGCACGGCA GGAGGTCGTA TATCAGTTTG GCCCGCTCCT GCCACTACCA CGGCGGTGAC
 723  AGTTGAAGGA ATGCGATGGG CACAAGCCTT CGCCCGTGAT CGGGCGGTAA TGTGGACGCT
 783  TCACATGGCG GAGAGCGATC ATGATGAGCG GATTCATGGG ATGAGTCCCG CCGAGTACAT
 843  GGAGTGTTAC GGACTCTTGG ATGAGCGTCT GCAGGTCGCG CATTGCGTGT ACTTTGACCG
 903  GAAGGATGTT CGGCTGCTGC ACCGCCACAA TGTGAAGGTC GCGTCGCAGG TTGTGAGCAA
 963  TGCCTACCTC GGCTCAGGGG TGGCCCCCGT GCCAGAGATG GTGGAGCGCG GCATGGCCGT
1023  GGGCATTGGA ACAGATAACG GGAATAGTAA TGACTCCGTA AACATGATCG GAGACATGAA
1083  GTTTATGGCC CATATTCACC GCGCGGTGCA TCGGGATGCG GACGTGCTGA CCCCAGAGAA
1143  GATTCTTGAA ATGGCGACGA TCGATGGGGC GCGTTCGTTG GGAATGGACC ACGAGATTGG
1203  TTCCATCGAA ACCGGCAAGC GCGCGGACCT TATCCTGCTT GACCTGCGTC ACCCTCAGAC
1263  GACTCCTCAC CATCATTTGG CGGCCACGAT CGTGTTTCAG GCTTACGGCA ATGAGGTGGA
1323  CACTGTCCTG ATTGACGGAA ACGTTGTGAT GGAGAACCGC CGCTTGAGCT TCTTCCCCC
1383  TGAACGTGAG TTGGCGTTCC TTGAGGAAGC GCAGAGCCGC GCCACAGCTA TTTTGCAGCG
1443  GGCGAACATG GTGGCTAACC CAGCTTGGCG CAGCCTCTAG GAAATGACGC CGTTGCTGCA
1503  TCCGCCGCCC CTTGAGGAAA TCGCTGCCAT CTTGGCGCGG CTCGGATTGG GGGCGGACA
1563  TGACCTTGAT GGATACAGAA TTGCCATGAA TGCGGCACTT CCGTCCTTCG CTCGTGTGGA
1623  ATCGTTGGTA GGTGAGGGTC GACTGCGGGC GCCAGCTTCC CGAAGAGGTG AAA
```

Figure 2A

```
  1  MQTLSIQHGTLVTMDQYRRVLGDSWVHVQDGRIVALGVHAESVPPPADRVIDARGKVVLP
 61  GFINAHTHVNQILLRGGPSHGRQFYDWLFNVVYPGQKAMRPEDVAVAVRLYCAEAVRSGI
121  TTINENADSAIYPGNIEAAMAVYGEVGVRVVYARMFFDRMDGRIQGYVDALKARSPQVEL
181  CSIMEETAVAKDRITALSDQYHGTAGGRISVWPAPATTTAVTVEGMRWAQAFARDRAVMW
241  TLHMAESDHDERIHGMSPAEYMECYGLLDERLQVAHCVYFDRKDVRLLHRHNVKVASQVV
301  SNAYLGSGVAPVPEMVERGMAVGIGTDNGNSNDSVNMIGDMKFMAHIHRAVHRDADVLTP
361  EKILEMATIDGARSLGMDHEIGSIETGKRADLILLDLRHPQTTPHHHLAATIVFQAYGNE
421  VDTVLIDGNVVMENRRLSFLPPERELAFLEEAQSRATAILQRANMVANPAWRSL
```

Figure 2B

```
                                                                    tg
   3   ctctagaagt tttattttt aattttcttt caaatacttc catctggaga caacaATGgA
  63   AACtCTCAGC ATCCAGCACG GTACCCTCGT CACtATGGAT CAGTACCGCA GAGTCCTTGG
 123   tGATAGCTGG GTTCACGTGC AGGATGGACG tATCGTCGCt CTCGGAGTGC ACGCCGAGTC
 183   aGTGCCTCCt CCAGCtGATC GtGTGATCGA TGCACGCGGC AAGGTCGTGT TACCCGGTTT
 243   CATCAATGCC CACACCCATG TGAACCAGAT CCTCCTGCGC GGAGGtCCCT CaCACGGaCG
 303   TCAATTCTAT GACTGGCTGT TCAACGTTGT GTATCCtGGA CAAAAGGCtA TGAGACCtGA
 363   GGACGTAGCt GTGGCaGTGA GGTTGTATTG TGCtGAAGCT GTGCGCAGCG GtATTACtAC
 423   tATCAACGAA AACGCCGATT CtGCCATCTA CCCAGGCAAC ATCGAGGCCG CtATGGCtGT
 483   CTATGGTGAG GTGGGTGTGA GGGTCGTCTA CGCCCGCATG TTCTTTGATC GtATGGACGG
 543   aCGCATTCAA GGtTATGTGG ACGCCTTGAA GGCTCGCTCT CCCCAAGTCG AACTGTGCTC
 603   aATCATGGAG GAAACtGCTG TGGCCAAAGA TCGtATCACA GCCCTGTCAG ATCAGTATCA
 663   TGGCACtGCA GGAGGTCGTA TATCAGTTTG GCCCGCTCCT GCCACTACCÅ CtGCaGTGAC
 723   AGTTGAAGGA ATGCGATGGG CACAAGCCTT CGCCCGTGAT CGtGCtGTtA TGTGGACtCT
 783   TCACATGGCt GAGAGCGATC ATGATGAGCG tATTCATGGt ATGAGTCCCG CCGAGTACAT
 843   GGAGTGTTAC GGACTCTTGG ATGAGCGTCT GCAGGTCGCt CATTGCGTGT ACTTTGACCG
 903   tAAGGATGTT CGaCTGCTGC ACCGCCACAA TGTGAAGGTC GCGTCaCAGG TTGTGAGCAA
 963   TGCCTACCTC GGCTCAGGtG TGGCCCCCGT GCCAGAGATG GTGGAGCGCG GCATGGCCGT
1023   GGGCATTGGA ACAGATAACG GcAATAGTAA TGACTCCGTA AACATGATCG GAGACATGAA
1083   GTTTATGGCC CATATTCACC GCGCtGTGCA TCGtGATGCt GACGTGCTGA CCCCAGAGAA
1143   GATTCTTGAA ATGGCtACaA TCGATGGtGC tCGTTCaTTG GGAATGGACC ACGAGATTGG
1263   TTCCATCGAA ACCGGCAAGC GCGCtGACCT TATCCTGCTT GACCTGCGTC ACCCTCAGAC
1323   GACTCCTCAC CATCATTTGG CtGCCACaAT CGTGTTTCAG GCTTACGGCA ATGAGGTGGA
1383   CACTGTCCTG ATTGACGGAA ACGTTGTGAT GGAGAACCGC CGCTTGAGCT TCTTCCCCC
1443   TGAACGTGAG TTGGCaTTCC TTGAGGAAGC tCAGAGCCGC GCCACAGCTA TTTTGCAGCG
1503   tGCtAACATG GTGGCTAACC CAGCTTGGCG CAGCCTCTAa aagagctcac gcc
```

Figure 3A

```
  1    MÊTLSIQHGTLVTMDQYRRVLGDSWVHVQDGRIVALGVHAESVPPPADRVIDARGKVVLP
 61    GFINAHTHVNQILLRGGPSHGRQFYDWLFNVVYPGQKAMRPEDVAVAVRLYCAEAVRSGI
121    TTINENADSAIYPGNIEAAMAVYGEVGVRVVYARMFFDRMDGRIQGYVDALKARSPQVEL
181    CSIMEETAVAKDRITALSDQYHGTAGGRISVWPAPATTTAVTVEGMRWAQAFARDRAVMW
241    TLHMAESDHDERIHGMSPAEYMECYGLLDERLQVAHCVYFDRKDVRLLHRHNVKVASQVV
301    SNAYLGSGVAPVPEMVERGMAVGIGTDNGNSNDSVNMIGDMKFMAHIHRAVHRDADVLTP
361    EKILEMATIDGARSLGMDHEIGSIETGKRADLILLDLRHPQTTPHHHLAATIVFQAYGNE
421    VDTVLIDGNVVMENRRLSFLPPERELAFLEEAQSRATAILQRANMVANPAWRSL
```

Figure 3B

TRANSGENIC PLANTS EXPRESSING BACTERIAL ATRAZINE DEGRADING GENE ATZA

GOVERNMENT FUNDING

The present invention was made with government support under Grant No. 95-34340-1605-04, awarded by the USDA, Cooperative State Research, Education, and Extension Service, National Research Initiative Competitive Grants Program, through a subcontract from Purdue University, No. 593-0220-04. The Government may have certain rights in this invention.

BACKGROUND

More than 8 million organic compounds are known and many are thought to be biodegradable by microorganisms, the principle agents for recycling organic matter on Earth. In this context, microbial enzymes represent the greatest diversity of novel catalysts. This is why microbial enzymes are predominant in industrial enzyme technology and in bioremediation, whether used as purified enzymes or in whole cell systems.

Effects of s-triazine Herbicide Use

Modern agricultural practices rely heavily on the use of herbicides to control weed populations. S-triazine (i.e., symetric triazine) herbicides, primarily atrazine and simazine, are widely used herbicides for selective control of broadleaf weeds and some grasses in a variety of crops. Since atrazine and other s-triazine herbicides biodegrade relatively slowly in soils, label directions for the use of atrazine restrict the types of crops that can be planted to prevent carryover problems in the next growing season. For example, alfalfa and soybeans are susceptible to atrazine concentrations in soil ranging from 0.09 mg/Kg to 0.53 mg/Kg, depending on the concentration of soil organic matter.

Numerous studies on the environmental fate of atrazine have shown that atrazine is a moderately persistant compound that is transformed to $CO_2$ very slowly, if at all, under aerobic or anaerobic conditions. It has a water solubility of 33 mg/l at 27° C. Its half-life (i.e., time required for half of the original concentration to dissipate) can vary from about 4 weeks to about 57 weeks when present at a low concentration (i.e., less than about 2 parts per million (ppm)) in soil. High concentrations of atrazine, such as those occurring in spill sites have been reported to dissipate even more slowly.

As a result of its widespread use, atrazine is sometimes detected in water in concentrations exceeding the maximum contaminant level (MCL) of 3 $\mu$g/l (i.e., 3 parts per billion (ppb)), a regulatory level that took effect in 1992. Point source spills of atrazine have resulted in levels as high as 25 ppb in some wells. Levels of up to 40,000 mg/l (i.e., 40,000 ppm) atrazine have been found in the soil at spill sites more than ten years after the spill incident. Point source spills and subsequent runoff can result in the presence of atrazine in surface, subsurface, and ground water.

While earlier studies have reported atrazine degradation only by mixed microbial consortia, more recent reports have indicated that several isolated bacterial strains can degrade atrazine. In fact, research groups have identified atrazine-degrading bacteria classified in different genera, including Rhodococcus sp. and Pseudomonas sp., from several different locations in the U.S. (e.g., Minnesota, Iowa, Louisiana, and Ohio) and Switzerland (Basel).

An atrazine-degrading bacterial culture, identified as Pseudomonas sp. strain ADP, ATCC No. 55464, was isolated and was found to degrade atrazine at concentrations greater than about 1,000 $\mu$g/ml under growth and non-growth conditions. See Mandelbaum, et al. (U.S. Pat. No. 5,508,193). Pseudomonas sp. strain ADP (Atrazine Degrading Pseudomonas) uses atrazine as a sole source of nitrogen for growth. The organism completely mineralizes the s-triazine ring of atrazine under aerobic growth conditions. That is, this bacteria is capable of degrading the s-triazine ring and mineralizing organic intermediates to inorganic compounds and/or ions (e.g., $CO_2$ and $NH_4$).

Herbicide Resistant Plants

More than 35 species of plants have been reported to be naturally resistant to s-triazine herbicides. Typically, these plants degrade atrazine via glutathione s-transferase reactions (i.e., the atrazine is conjugated to glutathione and subsequently degraded). Alternatively, these plants alter the protein atrazine binds, quinone-binding ($Q_B$) protein, which is a component of photosystem II in the chloroplast. Atrazine resistant weeds have been reported to have an altered $Q_B$ protein which has a 1000-fold reduced affinity for atrazine; however, these plants typically do not compete well in natural systems due to decreased photosynthesis efficiency. Furthermore, these plants do not degrade s-triazines. In the case of atrazine resistant plants, cross resistance to other s-triazine herbicides appears to be relatively common (Ottmeier, W. et al., *Pesticide Biochem. Physiol.*, 18, 357–367. (1982)). Thus, there is a need for methods to remove s-triazines from the environment.

SUMMARY OF THE INVENTION

In view of the occasional prevalence of s-triazines in the environment at levels above regulatory standards, there is a need in the art for methods to remediate, i.e., remove, s-triazines present in the environment, including soil and water. Thus, preferred aspects of the present invention provide transgenic plants that are resistant to s-triazine compounds, and methods of making and using such plants. Preferably these plants will degrade s-triazines, more preferably detoxify s-triazines, to more quickly reduce the occurrence of s-triazines in soil and water.

In a preferred embodiment, the present invention provides transgenic alfalfa plants that express a bacterial atrazine chlorohydrolase enzyme, AtzA. AtzA converts atrazine to hydroxyatrazine, which appears to have no herbicidal activity and which is relatively immobile in soil. Alfalfa has rooting characteristics which allow it to explore shallow and deep soils, thus it provides for the remediation of contaminated soils and possibility of remediating contaminated surface and subsurface water.

The present invention provides a transgenic plant including an exogenous coding region encoding an enzyme that imparts resistance to, and optionally degrades, at least one s-triazine. The s-triazine can be atrazine. The enzyme can dehalogenate at least one s-triazine, and if the s-triazine is atrazine, the atrazine can be converted to hydroxyatrazine.

The nucleotide sequence of the exogenous coding region can be nucleotides 58-1480 of SEQ ID NO:1. Alternatively, the complement of the nucleotide sequence of the exogenous coding region hybridizes to the nucleotide sequence set forth at nucleotides 58-1480 of SEQ ID NO:1 in a solution containing 250 mM $Na_2HPO_4$, pH 7.4, 2 ml/liter 0.5 M EDTA, pH 8.0, and 10 grams/liter bovine serum albumin at 65° C. for at least 4 hours, followed by three washes for twenty minutes each at 65° C. in a solution containing 2×SSC and 0.1% SDS.

The invention includes seeds of the transgenic plant, the progeny of a first or subsequent generation of the transgenic plant and the seeds thereof, and the seeds of the progeny of the first or subsequent generation of the transgenic plant. The plant can be a dicot, including an alfalfa plant, or a monocot, including a grass. A hybrid plant resistant to at least one s-triazine and an inbred plant resistant to at least one s-triazine, prepared from the transgenic plant, is also included in the present invention. In the transgenic plants, the exogenous coding region can impart resistance to levels of at least one triazine that inhibit the growth of a nontransgenic plant.

The invention is also directed at a method for degrading at least one s-triazine, including planting a plant in a composition containing an s-triazine wherein the plant degrades, and optionally detoxifies, at least one s-triazine in the composition, and growing the plant in the composition so that the plant degrades, and optionally detoxifies, at least one s-triazine. The plant can include an exogenous coding region that produces an enzyme capable of degrading, and optionally detoxifying, at least one s-triazine. The composition can include soil and/or water, and the plant can decrease the concentration of at least one s-triazine in the soil and/or the water. The at least one s-triazine can be selected from the group of atrazine, desethylatrazine, deisopropylatrazine, desethylhydroxyatrazine, desisopropylhydroxyatrazine, desethyldesisopropylatrazine, simazine, terbuthylazine, melamine, ammelide, ammeline, prometryn, ametryn, and propazine. The plant can be a dicot, including an alfalfa plant.

Another aspect of the invention is a method of imparting to a plant resistance to at least one s-triazine, including transforming a cell of a susceptible plant with a nucleic acid fragment including an exogenous coding region encoding an enzyme that degrades, and optionally detoxifies, at least one s-triazine, regenerating the transformed plant cell to provide a plant, and identifying a transformed plant which expresses the coding region so as to render the plant resistant to at least one s-triazine. The plant can be a dicot, including an alfalfa plant.

Definitions

"Nucleic acid fragment" as used herein refers to a polymeric form of nucleotides of any length, either ribonucleotides or deoxynucleotides, and includes both double- and single-stranded DNA (both genomic and plasmid) and both double- and single-stranded RNA. A polynucleotide fragment may include both coding and non-coding regions that can be obtained directly from a natural source (e.g., a microorganism), or can be prepared with the aid of recombinant or synthetic techniques. A "nucleic acid molecule" may be equivalent to this nucleic acid fragment or it can include this fragment in addition to one or more other nucleotides. For example, a nucleic acid molecule of the invention can be a vector, such as an expression or cloning vector.

"Polypeptide" as used herein refers to a polymer of amino acids and does not refer to a specific length of a polymer of amino acids. Thus, for example, the terms peptide, oligopeptide, protein, and enzyme are included within the definition of polypeptide. This term also includes post-expression modifications of the polypeptide, for example, glycosylations, acetylations, phosphorylations and the like.

"Host cells" refer to, for example, microorganisms, including prokaryotic (Eubacteria and Archea) microorganisms (e.g., E. coli and cyanobacteria), and eukaryotic microorganisms (e.g., Chlamydomonas) and plant cells that can be used as recipients for introduction of a vector.

"Coding region" refers to a nucleic acid fragment that encodes a polypeptide, usually via mRNA, when placed under the control of appropriate regulatory sequences. The boundaries of the coding region are generally determined by a translation start codon at its 5' end and a translation stop codon at its 3' end. "Exogenous coding region" refers to a foreign coding region, i.e., a coding region that is not normally present in a host cell. An exogenous coding region of the present invention typically contains no introns, but can be altered by methods known to the art of molecular biology to contain introns that are not present in the wild-type coding region. A coding region can be linked to a nucleic acid fragment encoding a transit or signal peptide, for instance a chloroplast transit peptide, that causes the polypeptide encoded by the coding sequence to be targeted to a particular compartment of a host cell.

"Regulatory region" refers to a nucleic acid fragment that regulates expression of a coding region to which a regulatory region is operably linked. Non-limiting examples of regulatory regions include promoters, enhancers, transcription initiation sites, translation start sites, translation stop sites, and terminators.

"Operably linked" refers to a juxtaposition wherein the components so described are in a relationship permitting them to function in their intended manner. A regulatory element is "operably linked" to a coding region when it is joined in such a way that expression of the coding region is achieved under conditions compatible with the regulatory region.

"Transformation" refers to the introduction of a nucleic acid fragment into a host cell, irrespective of the method used for introduction. An introduced nucleic acid fragment may be integrated into the host genomic DNA, or alternatively, maintained as a non-integrated vector, for example, as a plasmid.

The term "complement" and "complementary" as used herein, refers to the ability of two single stranded nucleic acid fragments to base pair with each other, where an adenine on one nucleic acid fragment will base pair to a thymine on a second nucleic acid fragment and a cytosine on one nucleic acid fragment will base pair to a guanine on a second nucleic acid fragment. Two nucleic acid fragments are complementary to each other when a nucleotide sequence in one nucleic acid fragment can base pair with a nucleotide sequence in a second nucleic acid fragment. For instance, 5'-ATGC and 5'-GCAT are complementary. The terms complement and complementary also encompass two nucleic acid fragments where one nucleic acid fragment contains at least one nucleotide that will not base pair to at least one nucleotide present on a second nucleic acid fragment. For instance the third nucleotide of each of the two nucleic acid fragments 5'-ATTGC and 5'-GCTAT will not base pair, but these two nucleic acid fragments are complementary as defined herein. Typically two nucleic acid fragments are complementary if they hybridize under certain conditions.

As used herein, "hybridizes," "hybridizing," and "hybridization" means that a single stranded nucleic acid fragment forms a noncovalent interaction with a complementary nucleic acid fragment under certain conditions, as described herein.

As used herein, the term "isolated" means that a nucleic acid fragment or polypeptide is either removed from its natural environment or synthetically derived. Preferably, the nucleic acid fragment or polypeptide is purified, i.e., essentially free from any other nucleic acid fragment or polypeptide and associated cellular products or other impurities.

"S-triazines," "s-triazine containing compounds" and "s-triazine herbicides" are used interchangeably and refer to compounds and herbicides containing, for example, atrazine (2-chloro-4-ethylamino-6-isopropylamino-1,3,5-s-triazine), desethylatrazine (2-chloro-4-amino-6-isopropylamino-s-triazine), deisopropylatrazine (2-chloro-4-ethylamino-6-amino-s-triazine), desethylhydroxyatrazine (2-hydroxy-4-amino-6-isopropylamino-s-triazine), desisopropylhydroxyatrazine (2-hydroxy-4-amino-6-isopropylamino-s-triazine), desethyldesisopropylatrazine (2-chloro-4,6-diamino-s-triazine), simazine (2-chloro-4,6-diethylamino-s-triazine), terbuthylazine (2-chloro-4-ethylamino-6-terbutylamino-s-triazine), melamine (2,4,6-triamino-s-triazine), ammelide (2,4-dihydroxy-6-amino-s-triazine), ammeline (2-hydroxy-4,6,-diamino-s-triazine), prometrym (N,N'-bis(1-methylethyl)-6-(methylthio)-1,3,5-triazine-2,4 diamine), ametryn (N-ethyl-N'-(1-methylethyl)-6-(methylthio)-1,3,5-triazine-2,4 diamine), and propazine (6-chloro-N,N'-bis(1-methylethyl)-1,3,5-triazine-2,4-diamine).

The phenotypes of "resistance," "herbicide resistant," and "herbicide tolerant" refer to the ability of a cell or plant to survive or continue to grow in the presence of certain concentrations of an s-triazine that typically kill or inhibit the growth of other cells or plants. Growth includes, for instance, photosynthesis, increased rooting, increased height, increased mass, and development of new leaves. Although there may be other mechanisms of providing resistance, the plants of the present invention degrade s-triazines. Preferably, degradation of an s-triazine causes an s-triazine to be detoxified, such that it is less herbicidal for plants.

"Degradation" of an s-triazine includes, for instance, removing or changing a portion of the molecule, such as opening the ring structure. Degradation of an s-triazine can result in a compound having increased toxicity to a plant, a compound having about the same toxicity to a plant as the nondegraded s-triazine, or a compound having lower toxicity to a plant. A degraded s-triazine having lower toxicity is referred to herein as detoxified.

"Transgene" as used herein refers to an exogenous coding region present in a host cell. A transgene is preferably transmitted to progeny cells.

"Transgenic" as used herein refers to any cell, cell line, tissue plant part or plant the genotype of which has been altered by the presence of an exogenous coding region. Typically, the exogenous coding region was introduced into the genotype by a process of genetic engineering, or was introduced into the genotype of a parent cell or plant by such a process and is subsequently transferred to later generations by sexual crosses or asexual propagation.

A "selectable marker" or "screenable marker" is a molecule that imparts a distinct phenotype to cells expressing the nucleic acid fragment encoding the marker and thus allow such transformed cells to be distinguished from cells that do not have the marker. A selectable marker confers a trait which one can 'select' for by chemical means, i.e., through the use of a selective agent (e.g., a herbicide, antibiotic, or the like). A screenable marker confers a trait which one can identify through observation or testing, i.e., by 'screening'.

"Hybrid" refers to progeny plants resulting from a cross between parental lines.

"Inbred" refers to progeny plants that are genetically homogeneous (homozygous) resulting from many generations of self crossing.

"Water" as used herein refers to surface water, subsurface water, and ground water. The terms surface water, subsurface water, and ground water are described in greater detail herein.

BRIEF DESCRIPTION OF THE FIGURES

FIG. 2. A. Nucleotide sequence (SEQ ID NO:1) of wild-type atzA. The start and stop codons are underlined. B. Amino acid sequence (SEQ ID NO:2) encoded by SEQ ID NO:1.

FIG. 3. A. Nucleotide sequence (SEQ ID NO:8) of an atzA coding region containing codons altered for expression in plants. Nucleotide differences between SEQ ID NO:8 and SEQ ID NO:1 are shown in lower case. The start and stop codons are underlined. B. Amino acid sequence (SEQ ID NO:9) encoded by SEQ ID NO:8. The amino acid difference between SEQ ID NO:9 and SEQ ID NO:2 at residue two is underlined.

DETAILED DESCRIPTION OF THE INVENTION

Figure 1:
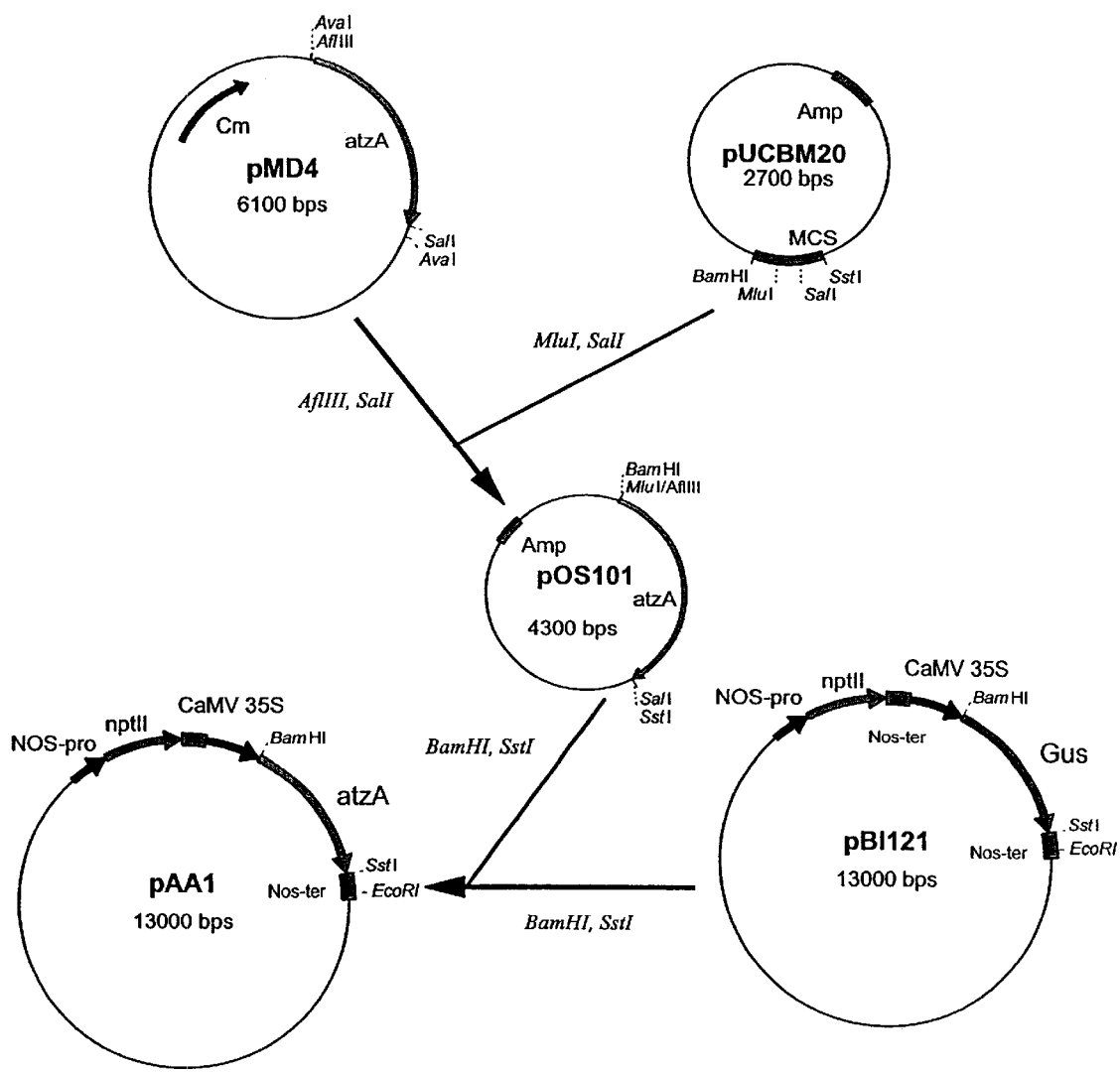
FIG. 1. Construction of plasmid pAA1. Abbreviations: NOS-pro, nopaline synthase promoter; Nos-ter, nopaline synthase termination signal; atzA, atrazine A coding region; nptII, neomycin phosphotransferase structural gene; bps, base pairs, GUS, glucuronidase coding region; MCS, multiple coding sequence; Amp, ampicillin resistance coding region; Cm, chloramphenicol resistance coding region; CaMV 35S, cauliflower mosaic virus 35S promoter.

One aspect of the present invention relates to plants that are resistant to at least one s-triazine. Preferably the plants degrade, more preferably detoxify, at least one s-triazine. Optionally, the plants include an exogenous coding region that imparts resistance to at least one s-triazine. Preferably, the exogenous coding region imparts an ability to degrade, preferably detoxify, at least one s-triazine. The present invention further relates to methods of imparting to a plant resistance to at least one s-triazine. An additional aspect of the invention are methods for degrading, preferably detoxifying, at least one s-triazine by planting an s-triazine degrading plant in a composition containing an s-triazine and growing the plant in the composition so that the plant degrades, preferably detoxifies, at least one s-triazine.

Important applications of the present invention include, but are not limited to, imparting to plants resistance to s-triazines, and degrading, preferably detoxifying, s-triazines present in the environment as a result of the application of herbicides. An advantage of preferred aspects of the invention is the decrease in the amount of s-triazines in the environment, including soil, and water, by environmental remediation of s-triazines. "Surface water" is water that is standing (e.g., a puddle) or moving (e.g., a stream) above ground level. "Subsurface water" is water present in soil and above the ground water. Subsurface water includes water that entered the soil as rain and water that originated from, for instance, a nearby waterway. "Ground water" is water that is located below the subsurface water and often supplies wells and springs. While not intending to be limiting, it is believed that plants of the present invention will remove s-triazines from surface water and subsurface water and also prevent s-triazines from moving into ground water. Thus, preferred aspects of the present invention can be used to decrease the amount of s-triazines which sometimes occur in drinking water.

Preferably, a plant resistant to at least one s-triazine grows in the presence of at least about 0.5 ppm, more preferably at least about 1.0 ppm, and most preferably at least about 10 ppm of at least one s-triazine. Generally speaking, a cell or plant can be resistant to s-triazines by at least three different mechanisms. For instance, the cell or plant can over-express a host-encoded molecule that an s-triazine interacts with and inhibits. Alternatively, a host-encoded molecule that an s-triazine interacts with and inhibits can be modified such that the host-encoded molecule is no longer inhibited by an s-triazine. Resistant plants have been isolated where a host-encoded molecule is altered such that a host-encoded molecule is no longer inhibited by an s-triazine. However, these plants displayed undesirable characteristics including, for instance, reduced growth. Thirdly, an s-triazine can be degraded so that it can no longer interact with a host-encoded molecule. Modifications to the chemical structure of s-triazines in the third category include the degradation of s-triazines by, for instance, dechlorination or deamination. Preferably, degradation of s-triazines results in detoxification, i.e., products that are less herbicidal for plants.

The polypeptides encoded by the exogenous coding regions of this invention are involved in the resistance of a plant or cell to at least one s-triazine. Preferably the polypeptides degrade, more preferably detoxify, at least one s-triazine. Preferably, the polypeptide is a wild type AtzA polypeptide, which can catalyze the dechlorination of s-triazines. As used herein, the coding region encoding a polypeptide capable of dechlorinating atrazine and originally identified in Pseudomonas sp. strain ADP, ATCC No. 55464 (U.S. Pat. No. 5,508,193, Mandelbaum) and expressed in *E. coli* is referred to as "atzA." atzA can be referred to in the art as the atzA structural gene. The polypeptide encoded by atzA is referred to as "AtzA." Examples of the cloned wild-type nucleotide coding region and the amino acid sequence derived from the nucleotide sequence of the coding region are provided as nucleotides 58-1480 of SEQ ID NO:1 and SEQ ID NO:2, respectively. The terms atrazine chlorohydrolase polypeptide, atrazine chlorohydrolase enzyme, atrazine chlorohydrolase, atrazine halidohydrolase enzyme, or simply AtzA, are used interchangeably, and refer to an atrazine chlorohydrolase enzyme involved in the degradation of atrazine and similar molecules as discussed herein.

Plants of the present invention are typically rendered resistant to s-triazine-containing compounds that include a chlorine atom and at least one alkylamino side chain. Such compounds have the following general formula:

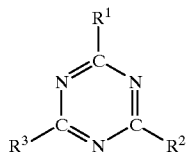

wherein $R^1$=Cl, $R^2$=$NR^4R^5$ (wherein $R^4$ and $R^5$ are each independently H or a $C_{1-3}$ alkyl group), and $R^3$=$NR^6R^7$ (wherein $R^6$ and $R^7$ are each independently H or a $C_{1-3}$ alkyl group), with the proviso that at least one of $R^2$ or $R^3$ is an alkylamino group. As used herein, an "alkylamino" group refers to an amine side chain with one or two alkyl groups attached to the nitrogen atom. Examples of such compounds include atrazine (2-chloro-4-ethlyamino-6-isopropylamino-1,3,5-s-triazine), desethylatrazine (2-chloro-4-amino-6-isopropylamino-s-triazine), deisopropylatrazine (2-chloro-4 -ethylamino-6-amino-s-triazine), desethylhydroxyatrazine (2-hydroxy-4-amino-6-isopropylamino-s-triazine), desisopropylhydroxyatrazine (2-hydroxy-4-amino-6-isopropylamino-s-triazine), desethyldesisopropylatrazine (2-chloro-4,6-diamino-s-triazine), simazine (2-chloro-4,6-diethylamino-s-triazine), terbuthylazine (2-chloro-4-ethylamino-6-terbutylamino-s-triazine), melamine (2,4,6-triamino-s-triazine), ammelide (2,4-dihydroxy-6-amino-s-triazine), ammeline (2-hydroxy-4,6,-diamino-s-triazine), prometrym (N,N'-bis(1-methylethyl)-6-(methylthio)-1,3,5-triazine-2,4diamine), ametryn (N-ethyl-N'-(1-methylethyl)-6-(methylthio)-1,3,5-triazine-2,4diamine), and propazine (6-chloro-N,N'-bis(1-methylethyl)-1,3,5-triazine-2,4-diamine).

An example of an AtzA s-triazine degradation activity is encoded by a coding region that is localized to a 21.5-kb EcoRI fragment, and more specifically to a 1.9-kb AvaI nucleic acid fragment, of the genome of Pseudomonas sp. ADP. Specifically, these nucleic acid fragments encode polypeptides involved in s-triazine dechlorination. The dechlorination of atrazine yields the less toxic and less herbicidal compound hydroxyatrazine. Hydroxyatrazine formation in the environment was previously thought to result solely from the chemical hydrolysis of atrazine. Previous reports suggest that the first step in atrazine degradation by environmental bacteria is dealkylation. Dealkylation produces a product that retains the chloride moiety and is likely to retain its toxicity in the environment. Thus, in contrast to these reports, AtzA dechlorinates atrazine and produces, in a one-step reaction that is amenable to exploitation in the remediation industry, a product that may pose less of a risk to s-triazine sensitive plants.

A nucleic acid fragment having a coding region encoding the wild-type AtzA amino acid sequence (SEQ ID NO:1 and SEQ ID NO:2, respectively) can be obtained from the atrazine-degrading bacterial culture identified as Pseudomonas sp. strain ADP. Other examples of polypeptides encoded by the coding regions of this invention include those that can be isolated from other organisms (see Wackett et al., U.S. patent application Ser. No. 08/546,793). For instance, using the nucleic acid fragment encoding the wild-type atzA nucleotide sequence, similar atrazine degrading enzymes have been identified in other bacteria. In fact, sequencing of the atzA coding region in the other bacteria demonstrated a similarity of at least 99% to the atzA sequence, suggesting little evolutionary drift. Coding regions having similarity to the atzA coding region could not be identified in the genomes of bacteria that did not metabolize atrazine.

The invention further includes a coding region that shares a significant level of similarity with the nucleotides of the coding region of SEQ ID NO:1 or SEQ ID NO:8. The similarity is referred to as percentage nucleic acid identity and is determined by aligning the residues of the two nucleic acid sequences (i.e., the nucleotide sequence of the candidate coding region and the nucleotide sequence of the coding region of SEQ ID NO:1 or SEQ ID NO:8) to maximize the number of nucleotides that they have in common along the lengths of their sequences; gaps in either or both sequences are permitted in making the alignment in order to maximize the number of shared nucleotides, although the nucleotides in each sequence must nonetheless remain in their proper order. A candidate coding region is the coding region being compared to a coding region present in SEQ ID NO:1 or SEQ ID NO:8. Preferably, two nucleic acid sequences are compared using the Basic BLAST search algorithm (using the blastn program and the nr database), release 2.0, available at the National Center for Biotechnology Information (seqsim.ncgr.org/) and described in S. F. Altschul et al. (*Nucl. Acids Res.,* 25, 3389–3402 (1997)). Preferably, the default values for all BLAST search parameters are used, including allowing the introduction of gaps. Preferably, two nucleotide sequences have at least about 85%, more preferably at least about 90%, even more preferably at least about 95%, most preferably at least about 99% identity.

Individual wild-type microorganisms can be screened for the presence of nucleotide sequences that are similar to the coding regions of the present invention. Screening methods include, for instance, hybridization of nucleic acid fragments immobilized on a membrane with a detectably labeled probe. Standard hybridizing conditions use hybridization buffer (250 mM $Na_2HPO_4$, pH 7.4, 2 ml/liter 0.5 M EDTA, pH 8.0, 10 grams/liter bovine serum albumin) containing 25 nanograms labeled probe DNA/ml hybridization buffer. Hybridization is allowed to occur at 65° C. for at least 4 hours. For low stringency hybridizations, the membrane is washed at 65° C., three times for twenty minutes each in a solution containing 2×SSC (1×SSC: 150 mM NaCl, 15 mM sodium citrate, pH 7.0) and 0.1% SDS. For high stringency hybridizations, the membrane is washed at 65° C., three times for twenty minutes each in a solution containing 0.1×SSC and 0.1% SDS. Preferably, a probe will hybridize to the nucleotide sequence set forth in SEQ ID NO:1 under the high stringency conditions. Generally the probe does not have to be complementary to all the nucleotides of a nucleic acid fragment as long as there is hybridization under the conditions described herein.

Preferred probes are nucleic acid fragments complementary to a coding region of the invention. For instance, a probe can comprise a consecutive series of nucleotides complementary to a portion of SEQ ID NO:1. A probe is typically no greater than about 1,400 bases and no less than about 10 bases. Typically a probe does not hybridize under conditions described herein with nucleotides that are not part of a coding region of the present invention. A particularly preferred probe is the approximately 600 base ApaI-PstI fragment that can be obtained from the plasmid pMD4 (De Souza et al., *Applied Environ. Microbiol.*, 61, 3373–3378 (1995)). Methods of detectably labeling a probe are well known to the art. The nucleic acid fragment that is identified by the probe is further analyzed using methods known to one of skill in the art to determine if it encodes a polypeptide imparting resistance to at least one s-triazine. Another method for screening individual microorganisms for the presence of nucleotide sequences that are similar to the coding regions of the present invention is the polymerase chain reaction (PCR). For instance, the primers 5'-CCATGTGAACCAGATCCT-3' (SEQ ID NO:6) and 5'-TGAAGCGTCCACATTACC-3' (SEQ ID NO:7) can be used to screen individual microorganisms for the presence of nucleotide sequences that are similar to the coding regions of the present invention.

The invention includes a polypeptide having a significant level of similarity with the amino acid sequence of SEQ ID NO:2. The similarity is referred to as percentage amino acid identity and is determined by aligning the residues of the two amino acid sequences (i.e., the amino acid sequence of the candidate polypeptide and the amino acid sequence of SEQ ID NO:2) to maximize the number of amino acids that they have in common along the lengths of their sequences; gaps in either or both sequences are permitted in making the alignment in order to maximize the number of shared amino acids, although the amino acids in each sequence must nonetheless remain in their proper order. A candidate polypeptide is the polypeptide being compared to a polypeptide present in SEQ ID NO:2. Preferably, two amino acid sequences are compared using the Basic BLAST search algorithm (using the blastp program and the nr database), release 2.0, available at the National Center for Biotechnology Information (http://seqsim.ncgr.org/) and described in S. F. Altschul et al. (*Nucl. Acids Res.*, 25, 3389–3402 (1997)). Preferably, the default values for all BLAST search parameters are used, including allowing the introduction of gaps. Preferably, a candidate polypeptide has greater than 70% identity, more preferably at least about 80% identity, most preferably at least about 90% identity with SEQ ID NO:2.

Alternatively, individual microorganisms can be screened for the presence of polypeptides that degrade, preferably detoxify, at least one s-triazine. The expression by a microorganism of a polypeptide of the invention can be assayed by, for instance, western blotting using an antibody that binds to the polypeptide expressed by the microorganism, the ability of the microorganism to reproduce in the presence of at least one s-triazine, or by measurement of degradation of at least one s-triazine.

Additional examples of polypeptides encoded by the coding regions of this invention include artificially constructed coding regions. For instance, gene shuffling, also termed recursive sequence recombination, has been used to construct coding regions encoding polypeptides that have similarity with the wild-type AtzA of SEQ ID NO:2. The construction of coding regions encoding polypeptides that impart resistance to an s-triazine is described in Wackett et al., U.S. application Ser. No. 09/155,036.

The polypeptides of the invention include a polypeptide having SEQ ID NO:2, or an active analog, active fragment, or active modification of SEQ ID NO:2. An active analog, active fragment, or active modification of a polypeptide having SEQ ID NO:2 is one that is able to degrade, preferably detoxify, at least one s-triazine. Active analogs of a polypeptide having SEQ ID NO:2 include polypeptides having amino acid substitutions that do not eliminate the ability to degrade at least one s-triazine. Substitutes for an amino acid may be selected from other members of the class to which the amino acid belongs. For example, nonpolar (hydrophobic) amino acids include alanine, leucine, isoleucine, valine, proline, phenylalanine, tryptophan, and tyrosine. Polar neutral amino acids include glycine, serine, threonine, cysteine, tyrosine, asparagine, and glutamine. The positively charged (basic) amino acids include arginine, lysine, and histidine. The negatively charged (acidic) amino acids include aspartic acid and glutamic acid. Examples of preferred conservative substitutions include Lys for Arg and vice versa to maintain a positive charge; Glu for Asp and vice versa to maintain a negative charge; Ser for Thr so that a free —OH is maintained; and Gln for Asn to maintain a free $NH_2$. Fragments of a polypeptide of the invention include a portion of the polypeptide containing deletions or additions of one or more contiguous or noncontiguous amino acids such that the resulting polypeptide will degrade at least one s-triazine. Modified polypeptides of the invention include polypeptides that are chemically or enzymatically derivatized at one or more constituent amino acids, including side chain modifications, backbone modifications, and N- and C-terminal modifications including acetylation, hydroxylation, methylation, amidation, and the attachment of carbohydrate or lipid moieties, cofactors, and the like. Active analogs, active fragments, and active modified polypeptides will degrade at least one s-triazine.

Alternatively, a polypeptide of the invention is encoded by a nucleic acid fragment, the complement of which hybridizes to the sequence of SEQ ID NO:1 under conditions of low stringency, preferably high stringency, or the nucleic acid fragment can have at least about 90%, more preferably at least about 95%, most preferably at least about 99% identity with SEQ ID NO:1.

Dicot and monocot plants that can be genetically manipulated can be used in the present invention. Preferably the plant is riparian and/or can grow along waterways, including switchgrass and cattails, grasses, and alfalfa. More preferably the plant is alfalfa, most preferably *Medicago sativa*. A plant that can be genetically manipulated is a plant into which exogenous coding regions can be introduced, expressed, stably maintained, and transmitted to subsequent generations of progeny. Genetic methods have been used to produce plants that are resistant to herbicides including, for instance, bialaphos, bromoxynil, and 2,4-dichlorphenoxyacetic acid.

The plants of the present invention can be used in methods for degrading, preferably detoxifying, at least one s-triazine in a composition. The methods include planting a plant that degrades at least one s-triazine in a composition containing an s-triazine. The plant is then allowed to grow in the composition so that the plant degrades at least one s-triazine. Preferably, the plant includes an exogenous coding region that produces a polypeptide that degrades at least one s-triazine. The composition can include soil and/or water. Preferably, the plant decreases the concentration of at least one s-triazine in the soil and/or the water. It is anticipated that the plants of the present invention can be planted in areas in or surrounding fields containing an s-triazine. It is also anticipated that the plants of the present invention can be planted in soil impacted by s-triazine containing water, for instance, water drained from fields containing s-triazine.

Transgenic plants may be obtained from transgenic seeds set by parental transgenic plants. Methods of making a transgenic plant of the invention typically involve the transformation of a cell of a plant sensitive to at least one s-triazine with a nucleic acid fragment comprising a coding region encoding a polypeptide that imparts resistance to at least one s-triazine. A nucleic acid fragment used to transform a host cell comprises an exogenous coding region encoding a polypeptide that imparts resistance to at least one s-triazine. The nucleic acid fragment is typically present on a vector. A vector can provide for further cloning (amplification of the nucleic acid fragment), i.e., a cloning vector, or for expression of the polypeptide encoded by the coding region, i.e., an expression vector. The term vector includes but is not limited to plasmid vector, viral vector, cosmid vector, and artificial chromosome vector. Optionally, the vector may be capable of existing independently or reversibly integrated into a chromosome (i.e., an episome). Typically, a vector will be a convenient vector capable of replication in a bacterial host, for instance *E. coli*. It is expected that bacterial host cells will be used for the construction of the nucleic acid fragment of the invention. In a plant cell, the vector can replicate independently, i.e., extrachromosomally, which can allow for high numbers of the vector to be maintained and potentially result in higher polypeptide production, or can be integrated into the genomic DNA. Preferably the vector is integrated into the genomic DNA of a plant cell. Vectors are preferably circular, but can be linear. Construction of suitable vectors employs standard ligation techniques known in the art. See, e.g., Sambrook et al, *Molecular Cloning: A Laboratory Manual.*, Cold Spring Harbor Laboratory Press (1989) or Ausubel, R. M., ed. *Current Protocols in Molecular Biology*, (1994).

An exogenous coding region is typically flanked by operably linked regulatory regions that regulate expression of the exogenous coding region in a transformed plant cell. A typical regulatory region operably linked to the exogenous coding region includes a promoter, i.e., a nucleic acid fragment that can cause transcription of the exogenous coding region, present 5' of the exogenous coding region. The invention is not limited by the use of any particular promoter, and a wide variety are known in the art. Plant-specific promoters are preferred. These include, but are not limited to, constitutive promoters, inducible promoters, and tissue-specific promoters. It can be, but need not be, heterologous with respect to the host. Promoters may be obtained from Ti- or Ri-plasmids, from plant cells, plant viruses or other hosts where the promoters are found to be functional in plants. Illustrative promoters include the octopine synthetase promoter, the nopaline synthase promoter, the manopine synthetase promoter, etc., as illustrative of promoters of bacterial origin functional in plants. Viral promoters include the cauliflower mosaic virus full length (CaMV35S) and region VI promoters, etc. Endogenous plant promoters include the ribulose-1,6-biphosphate (RUBP) carboxylase small subunit (ssu) promoter, the β-conglycinin promoter, the phaseolin promoter, the ADH promoter, GPAL2 promoter, GPAL3 promoter, heat-shock promoters, tissue specific promoters, e.g., promoters associated with fruit ripening, etc. Preferably, the promoter is a constitutive CaMV35S promoter.

Another typical regulatory region operably linked to the exogenous coding region includes a terminator, i.e., a nucleic acid fragment that can cause the termination of transcription of the exogenous coding region, present 3' of the exogenous coding region. The invention is not limited by the use of any particular terminator, and a wide variety are known in the art. Plant-specific terminators are preferred. These include, but are not limited to, a nopaline synthase terminator derived from the *Agrobacterium tumefaciens* Ti plasmid (Nos-ter).

The polypeptide produced by the exogenous coding region can be expressed in the cytoplasm of a plant cell. Alternatively, the polypeptide can be directed to an intracellular compartment within plant cells or to the extracellular environment. This can generally be achieved by joining a nucleic acid fragment containing a coding region encoding a transit or signal peptide sequence to the exogenous coding region. The nucleotides of the coding region encoding an amino terminal signal peptide is linked to the exogenous coding region so that the two coding regions are contiguous and in the same reading frame. The resultant transit, or signal, peptide will transport the polypeptide to a particular intracellular, or extracellular destination, respectively, and can then be post-translationally removed. Transit or signal peptides act by facilitating the transport of polypeptides through intracellular membranes, e.g., vacuole, vesicle, plastid and mitochondrial membranes, whereas signal peptides direct polypeptides through the extracellular membrane (for a review of plastid targeting peptides, see Heijne et al., *Eur. J. Biochem.*, 180, 535 (1989); Keegstra et al., *Ann. Rev. Plant Physiol. Plant Mol. Biol.*, 40, 471 (1989)). This is exemplified by the use of the rbcS (RuBISCO) transit peptide which targets polypeptides specifically to plastids. By facilitating transport of the polypeptide into compartments inside or outside the cell, these sequences can increase the accumulation of polypeptide encoded by the exogenous coding region.

A chloroplast transit peptide is typically 40 to 70 amino acids in length and functions post-translationally to direct a polypeptide to the chloroplast. An endogenous or an exogenous chloroplast transit peptide can be used. The transit peptide is cleaved either during or just after import into the chloroplast to yield the mature polypeptide.

Chloroplast transit peptide encoding sequences can be obtained from a variety of plant nuclear coding regions, so long as the products of the coding regions are expressed comprising an amino terminal transit peptide and transported into a chloroplast. Examples of plant gene products known to include such transit peptide sequences include, but are not limited to, the small subunit of ribulose bisphosphate carboxylase, ferredoxin, chlorophyll a/b binding polypeptide, chloroplast ribosomal polypeptides encoded by nuclear genes, certain heatshock polypeptides, amino acid biosynthetic enzymes such as acetolactate acid synthase, 3-enolpyruvylphosphoshikimate synthase, dihydrodipicolinate synthase, and the like. Alternatively, the nucleic acid fragment coding for the transit peptide may be chemically synthesized either wholly or in part from the known sequences of transit peptides such as those listed above.

Regardless of the source of the coding region encoding the transit peptide, it should include a translation initiation codon and an amino acid sequence that is recognized by and will function properly in chloroplasts of the host plant. Attention should also be given to the amino acid sequence at the junction between the transit peptide and the polypeptide encoded by the exogenous coding region where it is cleaved to yield the mature enzyme. Certain conserved amino acid sequences have been identified and may serve as a guideline. Precise fusion of the transit peptide coding region with the exogenous coding region may require manipulation of one or both nucleotide sequences to introduce, for example, a convenient restriction site. This may be accomplished by methods including site-directed mutagenesis, insertion of chemically synthesized oligonucleotide linkers, and the like.

Once obtained, the chloroplast transit peptide sequence can be appropriately linked to the promoter and the exogenous coding region in the nucleic acid fragment using standard methods. Briefly, a plasmid containing a promoter functional in plant cells and having multiple cloning sites downstream from the promoter can be constructed using techniques known to the art. The chloroplast transit peptide sequence can be inserted downstream from the promoter using restriction enzymes. The exogenous coding region can then be inserted immediately downstream from and in frame with the 3' terminus of the chloroplast transit peptide sequence so that the chloroplast transit peptide is linked to the amino terminus of the polypeptide encoded by the exogenous coding region. Once formed, the nucleic acid fragment can be subcloned into other plasmids or vectors.

Bacterial coding regions may not always have the appropriate codons for efficient expression in plants. Thus it can be advantageous to increase translational efficiency of a coding region of the present invention by altering the nucleotide sequence of codons such that the codons are recognized by the plant. Codons preferred in plants can be found in Murray et al. (*Nucl. Acids. Res.,* 17, 477–498 (1989)). Individual nucleotides of a nucleic acid fragment can be altered using techniques well known to the art, including, for instance, gene assembly (Stemmer et al. (*Gene,* 164, 49–53 (1995)). The nucleotide sequence of an atzA coding region altered to increase translational efficiency of the coding region in a plant is shown in FIG. 3.

The nucleotides that make up and surround the initiation and stop codons of a coding region can optionally be altered to increase translational efficiency (Gallie, *Annu. Rev. Plant Physiol. Plant Mol. Biol.,* 44, 77–105 (1993)). Preferably, the initiation codon and surrounding sequences includes ACAACA<u>ATG</u>GCT, where the underlined ATG codon is the translation initiation codon. Preferably, the stop codon and surrounding sequences includes <u>TAA</u>A, where the underlined TAA codon is the translation stop codon. Optionally, a leader sequence can be inserted between the initiation codon and promoter. Examples of leader sequences that could be used are present in Gallie et al. (*Nucl. Acids Res.,* 15, 3257–3273 (1987)), and Jobling et al. (*Nature,* 325, 622–625 (1987)).

In order to improve the ability to identify transformants, a coding region encoding a selectable or screenable marker can be present on the nucleic acid fragment in addition to the exogenous coding region. Possible selectable markers for use in connection with the present invention include, but are not limited to, neo, which codes for kanamycin resistance and can be selected for using kanamycin, G418, and the like; bar, which codes for bialaphos resistance and can be selected for using bialaphos and the like; a coding region which encodes an altered EPSP synthase polypeptide thus conferring glyphosate resistance; bxn, from *Klebsiella ozaenae* which codes for resistance to bromoxynil; a mutant acetolactate synthase coding region which confers resistance to imidazolinone, sulfonylurea or other ALS-inhibiting chemicals; a DHFR coding region that confers resistance to methotrexate; a dalapon dehalogenase coding region that confers resistance to the herbicide dalapon; a mutated anthranilate synthase coding region that confers resistance to 5-methyl tryptophan; or an exogenous coding region of the present invention encoding resistance to at least one s-triazine. Where an altered EPSP synthase coding region is employed, additional benefit may be realized through the incorporation of a suitable chloroplast transit peptide (European Patent Application 0 218 571 1987). The coding regions of the present invention can also be used as a selectable marker for introducing other genes into different intracellular compartments, preferably into chloroplasts (see, e.g., Daniell et al. (*Nature Biotechnol.,* 16, 345–348 (1998)).

Screenable markers that may be employed include, but are not limited to, a β-glucuronidase or uidA coding region (GUS) which encodes an enzyme for which various chromogenic substrates are known; an R-locus coding region, which encodes a product that regulates the production of anthocyanin pigments (red color) in plant tissues (Dellaporta et al., in *Chromosome Structure and Function,* pp. 263–282 (1988)); a β-lactamase coding region (Sutcliffe, *Proc. Natl. Acad. Sci. USA,* 75, 3737 (1978)), which encodes an enzyme for which various chromogenic substrates are known (e.g., PADAC, a chromogenic cephalosporin); a xylE coding region (Zukowski et al., *Proc. Natl. Acad. Sci. USA,* 80, 1101 (1983)) which encodes a catechol dioxygenase that can convert chromogenic catechols; an α-amylase coding region (Ikuta et al., *Biotech.,* 8, 241 (1990)); a tyrosinase coding region (Katz et al., *J. Gen. Microbiol.* 129, 2703 (1983)) which encodes an enzyme capable of oxidizing tyrosine to DOPA and dopaquinone which in turn condenses to form the easily detectable compound melanin; a β-galactosidase coding region, which encodes an enzyme for which there are chromogenic substrates; a luciferase (lux) coding region (Ow et al., *Science,* 234, 856 (1986)), which allows for bioluminescence detection; an aequorin coding region (Prasher et al., *Biochem. Biophys. Res. Comm.,* 126, 1259 (1985)), which may be employed in calcium-sensitive bioluminescence detection, or a green fluorescent protein coding region (Niedz et al., *Plant Cell Reports,* 14, 403 (1995)).

A variety of techniques are available for the introduction of the nucleic acid fragment into a host cell. However, the particular manner of introduction of the nucleic acid fragment into the host cell is not critical to the practice of the present invention, and methods which provide for efficient transformation may be employed. Transformation of bacterial host cells can be accomplished by, for instance, electroporation or calcium chloride treatment. Transformation of cyanobacteria can be accomplished using the techniques described by Elhai et al. (*Methods Enzymol.,* 167, 747–753 (1988)). Transformation of Chlamydomonas can be accomplished using the techniques described by Przibilla et al. (*Plant Cell*, 3, 169 (1991)). For the introduction of the nucleic acid fragment into a plant cell, in addition to transformation using plant transformation vectors derived from the tumor-inducing (Ti) or root-inducing (Ri) plasmids of Agrobacterium, alternative methods can be used. Such methods may include, for example, the use of liposomes, transformation using viruses or pollen, chemicals that increase the direct uptake of DNA (Paszkowski et al., *EMBO J.*, 3, 2717 (1984)), microinjection (Crossway et al., *Mol. Gen. Genet.*, 202, 179 (1985)), electroporation (Lee et al., *Proc. Natl. Acad. Sci. USA*, 82, 824 (1985)), or high-velocity microprojectiles (Klein et al., *Nature*, 327, 70 (1987)).

The choice of plant tissue source or cultured plant cells for transformation will depend on the nature of the host plant and the transformation protocol. Useful tissue sources include callus, suspension culture cells, protoplasts, leaf segments, stem segments, tassels, pollen, embryos, hypocotyls, tuber segments, meristematic regions, and the like. The tissue source is regenerable, in that it will retain the ability to regenerate whole, fertile plants following transformation. The transformation is carried out under conditions directed to the plant tissue of choice. Buffers and media used will also vary with the plant tissue source and transformation protocol.

Following exposure to the nucleic acid fragment under the appropriate conditions, the plant cells or tissue may be cultivated for varying lengths of time prior to selection, or may be immediately exposed to a selective agent such as those described hereinabove. Protocols involving exposure to Agrobacterium may also include an agent inhibitory to the growth of the Agrobacterium cells. Commonly used compounds are antibiotics such as cefotaxime and carbenicillin. The media used in the selection may be formulated to maintain transformed callus or suspension culture cells in an undifferentiated state, or to allow production of shoots from callus, leaf or stem segments, tuber disks, and the like.

Cells or callus observed to be growing in the presence of normally inhibitory concentrations of the selective agents are presumed to be transformed and may be subcultured several additional times on the same medium to remove non-resistant sections. The cells or calli can then be assayed for the presence of the nucleic acid fragment, or may be subjected to known plant regeneration protocols. In protocols involving the direct production of shoots, those shoots appearing on the selective media are presumed to be transformed and may be excised and rooted, either on the selective medium suitable for the production of roots, or by simply dipping the excised shoot in a root-inducing compound and directly planting it in vermiculite.

The expression by a plant of a transgene imparting resistance to at least one s-triazine can be assayed by, for instance, western blotting using an antibody that binds to the polypeptide expressed by the transgene, ability of the transgenic plant to root and/or grow in the presence of at least one s-triazine, or by measurement of degradation of at least one s-triazine.

The mature transgenic plants can be self crossed to produce a homozygous inbred plant. The inbred plant produces seed containing the exogenous coding region. These seeds can be grown to produce plants that would produce the selected phenotype, resistance to at least one s-triazine. Progeny of a first or subsequent generation of the transgenic plants of the invention and the seeds of such progeny are also included within the scope of the invention, provided that these progeny and seed comprise the exogenous coding region. The usefulness of the plants is greatest if many different hybrid combinations are available. Thus, it may be necessary to breed resistance to at least one s-triazine into many parental lines so that many hybrid combinations can be produced.

EXAMPLES

The present invention is illustrated by the following examples. It is to be understood that the particular examples, materials, amounts, and procedures are to be interpreted broadly in accordance with the scope and spirit of the invention as set forth herein.

Example 1

Construction of a Transgenic Alfalfa Containing the AtzA Coding Region

Bacterial strains: Competent *Escherichia coli* DH5α (GIBCO BRL, Ltd., Gaithersburg, Md.) was used as recipient in transformation experiments. Transformation was done by the classical $CaCl_2$ method as described by Maniatis et al., *Molecular Cloning: A Laboratory Manual*, Cold Spring Harbor Laboratory Press, Cold Spring Harbor, N.Y. (1982). *Agrobacterium tumefaciens* LBA 4404 (Ooms et al., *Plasmid*, 7, 15–29 (1982)) was used to introduce the t-DNA region into alfalfa. Plasmid pAA1 was introduced into *A. tumefaciens* LBA4404 from *E. coli* DH5 in a three parental mating using *E. coli* 2013 as helper (Leong et al., *J. Biol. Chem.*, 257, 8724–8730 (1982)).

Antibiotics: Rifampicin (Rif), 30 μg/ml; kanamycin (Km), 50 μg/ml; ampicillin (Ap), 50 μg/ml; chloramphenikol (Cm), 30 μg/ml were used for selecting transformant and transconjugant bacteria. For selection for transgenic alfalfa, 25 μg/ml Km and 500 μg/ml ticarcillin (Tc) were applied.

Restriction digestion and cloning: Restriction enzymes were purchased from New England Biolabs Inc (Beverly, Mass.). and GIBCO-BRL Ltd (Gaithersburg, Md.). Restriction enzymes were used according to the supplier's instructions. Cloning and other DNA and RNA manipulations were carried out according to standard procedures as described by Maniatis et al., *Molecular Cloning: A Laboratory Manual*, Cold Spring Harbor Laboratory Press, Cold Spring Harbor, N.Y. (1982).

Plant material and plant transformation: For transformation the embryogenic line of *Medicago sativa* cv. Regen SY was used (Bingham, *Crop Sci.*, 31, 1098 (1991). Leaves were surface sterilized in 70% ethanol for 10 seconds, followed by treatment in a solution containing 20% bleach and 0.05% Tween 20 for 90 seconds. Leaf disks were inoculated with *Agrobacterium tumefaciens* LBA4404 carrying pAA1 for a week on B5h plates then washed and transferred onto B5h medium containing Km and Tc. After two weeks calli were transferred onto B5h medium with Km and Tc but without hormones. Embryos formed on this plates were transferred to MMS plates with Km and Tc. Individual regenerating plantlets were transferred to MMS medium with Km and Tc in Magenta box. After full development transgenic plants were moved to Magenta containers (Sigma Chemical, St. Louis, Mo.) in a growth chamber. The composition of B5h and MMS media are described by Gamborg et al., *Experimental Cell Research*, 50, 151–158 (1968); Brown et al., *Plant Cell Tissue Organ Culture*, 4, 107–114 (1985); and Austin et al., *Euphytica*, 85, 381–393 (1995). Plants were grown in growth chambers at 22° C. under a 16 hour photoperiod. Transgenic plants were treated according to the Federal Containment Guidelines (NIH Guidelines for Research Involving Recombinant DNA Molecules, published in Federal Register, Jul. 5, 1994 (59 FR 34496)).

Atrazine plate clearing assays: Potential atzA-carrying *A. tumefacians* LBA4404 strains were grown on minimal LB media containing atrazine as the sole nitrogen source and assayed for their ability to clear atrazine as previously described (Mandelbaum et al., *Appl. Environ. Microbiol.*, 59(6), 1695–701 (1993)). Agar plates containing atrazine were cloudy as a result of particulate atrazine in the medium, enabling visual inspection of clearing zones around atrazine-degrading colonies. Minimal LB media contained, per liter of deionized water: 1.6 grams $K_2HPO_4$, 0.4 gram $KH_2PO_4$, 0.2 gram $MgSO_4.7H_2O$, 0.1 gram NaCl, 0.02 gram of $CaCL_2$, 1 gram sucrose, 1 gram sodium citrate, 2.5 ml atrazine stock solution, 20 ml salt stock solution, 20 ml vitamin stock solution, and 22% (wt/vol) Noble agar (Difco Laboratories, Detroit, Mich.). The salt stock contained, per liter of deionized water: 2.5 grams EDTA, 11.1 grams $ZnSO_4$, 5.0 grams $FeSO_4$, 1.54 grams $MnSO_4$ $H_2O$, 0.4 gram $CuSO_4.5H_2O$, 0.25 gram $Co(NO_3)_2.6H_2O$, 0.18 gram $Na_2B_4O_7.10H_2O$, and 5.0 ml concentrated $H_2SO_4$ to retard precipitation of salts. The vitamin stock solution contained, per liter of deionized water: 5 mg thiamine-HC1, 2 mg biotin, 2 mg folic acid, 10 mg nicotinamide, and 10 mg pyridoxine-HC1. The atrazine stock solution was prepared in methanol (20 mg/ml) and was vigorously shaken for several hours prior to incorporation into the medium. The pH of the media was adjusted to 7.3. Atrazine was obtained from Chem Service (West Chester, Pa.).

DNA and RNA gel blot analysis: Genomic DNA was extracted from 200 mg young leaves of untransformed and transgenic *Medicago sativa* cv. Regen SY plants using the DNeasy Plant Mini Kit (QIAgene Inc., Valencia, Calif.) according to the supplier's instructions. Genomic DNAs (15 μg) were digested with EcoRI and HindIII restriction endonucleases. Digested DNA was separated on 0.8% agarose gel and transferred onto NYTRAN PLUS nylon filter (Schleicher and Schuell, Keene, N.H.)). Total RNA was isolated from 100–120 mg young leaves and 120–320 mg root tissue respectively of untransformed and transgenic alfalfa using the RNeasy Plant Mini Kit (QIAgene Inc.). Total RNAs (15 μg) were separated on 1.2% agarose-formaldehyde gel and blotted onto Zeta-Probe membrane (Millipore, Bedford, Mass.)). Blotting, hybridization and washing were performed according to the procedures suggested for the filters by the suppliers. The random-primed 1.6 kb BamHI-EcoRI fragment of pAA1 carrying the atzA coding region (see FIG. 1) was used as hybridization probe for both DNA and RNA blots.

DNA amplification: PCR amplifications were performed in 50 μl reaction mixture (50 mM KCl, 10 mM Tris-HCl (pH 8.4), 1.5 mM $MgCL_2$, 200 μM of each dNTP, about 0.25 μM primer, 2.5 U Taq polymerase (GIBCO BRL, Ltd., Gaithersburg, Md.) and 50 ng template DNA). The PCR reaction was carried out in 30 cycles with the following steps: 1 minute at 65° C., 1 minute at 72° C., 30 seconds at 94° C. The amplification process was begun with a 3 minute denaturation step at 94° C. and ended with a 4 minute extension step at 72° C. Two atzA specific primers (AtzA1O and AtzA2H) were used for amplification. The sequence of the primers were the following: AtzA1O, 5'-GGCTGTCTATGGTGAGGTG-3' (SEQ ID NO:3); AtzA2H, 5'-CCGAGGTAGGCATTGCTCA-3' (SEQ ID NO:4).

Western Blotting: Protein was extracted from young root by grinding 100–400 mg tissue in extraction buffer (100 mM MES, pH 6.8, 15% ethylene glycol, 2% 2-mercaptoethanol, 100 mM sucrose, 10 μg/ml phenylmethylsulfonyl fluoride (PMSF)) at 0° C. Debris were removed by centrifugation at 14,000 rpm in an Eppendorf centrifuge at 4° C. Protein concentration was determined by the BioRad protein determination kit of BioRad (Hercules, Calif.). Protein from each sample (20 μg) was precipitated by 10% trichloroacetic acid and re-suspended in sample buffer (10% sucrose, 4% sodium dodecyl sulfate (SDS), 5% 2-mercaptoethanol, 67 mM Tris, pH 6.7). Before loading samples were incubated for 5 minutes at 100° C. Proteins were separated on a 12.5% denaturing polyacrylamide gel, electrotransferred onto a nitrocellulose filter (Schleicher and Schuell) and hybridized to AtzA specific polyclonal antibody in 1:2000 dilution. Polyclonal antibody was produced as described in U.S. application Ser. No. 08/546,793 (Wackett et al.). Primary antibodies were detected by goat anti-rabbit IgG alkaline phosphatase conjugate (Sigma, St. Louis, Mo.) as secondary antibody. The presence of alkaline phosphatase was detected by the alkaline phosphatase BCIP/NBT color development kit from BIO-RAD. For molecular mass determination the Kaleidoscope Prestained Standards from BIO-RAD was used.

Results and Discussion

Construction of the plant vector pAA1 carrying atzA: The AflIII-SalI fragment containing the bacterial atzA (de Souza et al., *Appl. Environ. Microbiol.*, 61, 3373–3378 (1995)) (SEQ ID NO:1) was cloned into the MluI-SalI site of plasmid pUCBM20 (Boehringer Mannheim, Indianapolis, Ind.) to generate plasmid pOS101. The BamHI-SstI atzA-containing fragment was cloned into the BamHI-SstI site of plasmid pBI121(ClonTech, Palo Alto, Calif.) to generate plasmid pAA1. Plasmid pAA1 was sequenced using primers OS1, 5'-ACCCCAGAGAAGATTCTTGAAATGGCTACAATC GATGGTGCTCGTTCATTGGG-3' (SEQ ID NO:10) and OS19, 5'-ATTGACGTCCGTGTGAGGGACCTCCGCGCAGGA GGATCTGGTTCACATG GGTGTGGGCA-3' (SEQ ID NO:5). Sequence analysis confirmed that pAA1 carries the CaMV35S promoter in front of atzA. *E. coli* DH5α carrying pAA1 showed clearing on LB plates containing atrazine at an atrazine concentration of 500 parts per million.

Plasmid pAA1 was introduced into *A. tumefaciens* LBA4404. Plasmid DNA analysis from *A. tumefaciens* transconjugants revealed that they carried plasmid pAA1. These transconjugants showed clearing of atrazine on LB plates.

Introducing atzA into alfalfa: Plasmid pAA1 carries atzA under the control of the CaMV35S promoter in the T-DNA segment in addition to the neomycin phosphotranspherase coding region which is used for selection for transformed cells. This t-DNA segment was delivered into *M. sativa* cv. Regen SY by *A. tumefaciens* LBA4404. Out of 45 inoculated leaf disks, 9 plants (T2, T4, T5, T6, T17, T19, T23, T28, T31) were regenerated to whole plants. These plants, and the untransformed control (SY), were tested for atrazine tolerance and characterized molecularly for the presence of transformed DNA, transcripts, the AtzA protein, as well as for the conversion of the atrazine to hydroxyatrazine.

Atrazine tolerance of the transgenic alfalfa plants: Sterile (germ free) cuttings from the transgenic and control plants were tested for rooting and growth in the presence of different concentration of atrazine on sugar-free and hormone-free B5h medium in Magenta boxes. Under these conditions plant growth depends on photosynthesis for production of energy and carbon. Atrazine, a potent inhibitor of photosynthesis, inhibits rooting, growth and plant development if atrazine reaches an effective threshold. Control plant cuttings did not root or grow in the presence of $5 \times 10^{-7}$ M or greater concentration of atrazine. On the other hand, all 9 transformed lines did root and showed normal growth (e.g., development of new leaves) in the presence of $2 \times 10^{-6}$ M atrazine. This result indicated that the transformed plants tolerated a higher concentration of atrazine than wild type plants.

Detection of atzA in the transgenic plants: A 510 base pair atzA-specific fragment could be amplified from 50 ng total genomic DNA isolated from the transformants. This 510 base pair fragment could not be amplified from template DNA of the control untransformed alfalfa. This result indicated that atzA was present in the transfomants.

Because PCR amplification does not give any information about the copy number and the position of the inserted DNA, a DNA-DNA hybridization experiment was perfomed. Total DNA (15 μg) from the untransformed and transgenic plants was digested by EcoRI and HindIII enzymes, separated on an agarose gel and transferred to a nylon membrane. The blot was probed with the 1.6 kb EcoRI BamHI fragment of pAA1 which carries atzA. The autoradiogram revealed that all transformants but the control SY plant contained sequences homologous to atzA. Interestingly, 8 transformants had a similar, approximately 2.3 kb EcoRI fragment while transformant T23 had an approximately 8 kb EcoRI fragment. The expected size of an EcoRI fragment in a genuine transformant is more than 5 kb, since the distance between the right and left border of the T-DNA in pAA1 is about 5 kb. Similarly, 8 transformants having the similiar 2.3 kb EcoRI fragment had a similar HindIII fragment of about 8 kb. Transformant T23 displayed two hybridizing HindIII fragments of 3.1 and 3.9 kb, respectively. The expected size of a HindIII fragment is more than 2.7 kb, because the HindIII site is 2.7 kb away from the left border. It was concluded that T23 was a genuine transformant because the actual hybridizing EcoRI and HindIII fragments are longer than the expected fragment size. It is not certain whether one or two independent insertions took place, because there is only one strongly hybridizing EcoRI fragment observable. On the other hand the two HindIII fragments can be explained by partial digestion.

Detection of the atzA transcript in the transformants: Total RNA was isolated from young leaf and root tissue from the untransformed and transformed alfalfa plants. Total RNA (15 μg) was separated on agarose-formaldehyde gel and transferred onto nylon filters and hybridized with the atzA specific probe (the probe was the same as it is used for the DNA-DNA hybridization). A 1.5 kb transcript was visible in both leaf and root tissue of transformant T23. No transcript was detectable in either tissue of the other transformants.

Detection of the AtzA protein by Western analysis: Proteins (20 μg) extracted from root tissue were separated on a 12.5% polyacrylamide gel electrophoresis and transferred to a nitrocellulose filter. AtzA protein was detected by a rabbit anti-AtzA polyclonal antibody. The approximately 60 kD AtzA protein was detectable in small amounts in all transformed plants but not in the control untransformed alfalfa. This result demonstrates that the AtzA specific protein was present in all the transformed plants, even though the AtzA transcript was detected in only one transformant, T23. The presence of the AtzA protein in the transformants could be responsible for the enhanced level of resistance to atrazine in the transformants.

Example 2

Degradation of atrazine by transgenic alfalfa

Atrazine tolerance by whole plants: T23 whole plants were vegetatively propagated by stem cuttings in 25-cm plastic cones containing a 2:1 vermiculite and sand mixture. Plants were grown in a growth chamber at 22° C. under a 16 hour photoperiod. Healthy 15–25 cm plants were removed from the cone containers and their roots were thoroughly washed with sterile water. Once the roots were completely free of all soil, the plants were inserted into 16 oz. Mason jars fitted with a rubber stopper that allowed the roots to remain submerged in hydroponic nutrient solution (Wych et al., *Plant Physiol.*, 62, 443–448 (1978)) while the remainder of the plant grew above the jar. Plants were aerated constantly by fish tank air stones submerged in the nutrient solution and connected to rubber tubing which passed through a hole in the rubber stopper and was connected to a 5 horsepower air compressor.

After allowing the plants to acclimate to hydroponic conditions for 4 days, the hydroponic nutrient solution was replaced with 400 ml of hydroponic nutrient solution plus 0.2 ppm (0.2 ug/ml) atrazine and the plants were allowed to grow for an additional 5 days. After 5 days, the remainder of the atrazine-containing nutrient solution was removed from the Mason jars and the volume was brought back up to 400 ml. Fifty ml aliquots were extracted with liquid-liquid partitioning and the remaining atrazine levels were quantified by gas chromatography as previously described (Widmer et al., *J. Environ. Sci. Health*, 28 (1), 19–28 (1993)).

Results in Table 1 show that the transgenic alfalfa plants expressing bacterial AtzA removed 40% more atrazine from the plant growth solution than did the wild-type SY control plants.

TABLE 1

Relative Atrazine Removal by Transgenic Alfalfa Plants Expressing Bacterial atzA.

| Plant | Relative Percent Removal[a] |
| --- | --- |
| No Plant Control | 0 |
| Wild-Type Regan SY Control | 17.9 |
| Transgenic Alfalfa T23 | 58.4 |

[a]Relative to no plant controls.

The complete disclosures of all patents, patent applications, publications, and nucleic acid and protein database entries, including for example GenBank accession numbers and EMBL accession numbers, that are cited herein are hereby incorporated by reference as if individually incorporated. Various modifications and alterations of this invention will become apparent to those skilled in the art without departing from the scope and spirit of this invention, and it should be understood that this invention is not to be unduly limited to the illustrative embodiments set forth herein.

Sequence Listing Free Text

SEQ ID NOs:3–7 and 10: Oligonucleotide primer

SEQ ID NO:8: An atzA coding region modified to contain codons to optimize expression in plants SEQ ID NO:9: The protein encoded by SEQ ID NO:8.

What is claimed is:

1. A transgenic plant transformed with an isolated polynucleotide comprising a nucleotide sequence encoding a Pseudomonas spp. atrazine chlorohydrolase enzyme.

2. The transgenic plant of claim 1 wherein the nucleotide sequence comprises nucleotides 58–1408 of SEQ ID NO: 1.

3. A transgenic plant transformed with an isolated polynucleotide comprising a nucleotide sequence encoding an s-triazine dehalogenase, wherein a complement of said polynucleotide hybridizes to a polynucleotide having the nucleotide sequence set forth in nucleotides 58–1480 of SEQ ID NO: 1 in a solution containing 250 mM $Na_2HPO_4$, pH 7.4, 2 ml/liter 0.5 M EDTA, pH 8.0 and 10 grams/liter bovine serum albumin at 65° C. for at least 4 hours, followed by three washes for twenty minutes each at 65° C. in a solution containing 0.1×SSC and 0.1% SDS.

4. A transgenic plant transformed with an isolated polynucleotide comprising a nucleotide sequence encoding the amino acids sequence of SEQ ID NO: 2.

5. A method for degrading at least one s-triazine comprising:

(a) planting the transgenic plant of claim 1, 3 or 4 in a composition comprising at least one s-triazine; and (b) growing the transgenic plant in the composition so that the plant dehalogenates the at least one s-triazine, wherein the plant decreases the concentration of the at least one s-triazine in the composition.

6. The method of claim 5 wherein at least one s-triazine is selected from the group consisting of atrazine, desethylatrazine, deisopropylatrazine, desethylhydroxyatrazine, desisopropylhydroxyatrazine, desethyldesisopropylatrazine, simazine, terbuthylazine, melamine, ammelide, ammeline, prometryn, ametryn, and propazine.

7. The method of claim 5, wherein the plant is a dicot.

8. The method of claim 7, wherein the plant is an alfalfa plant.

* * * * *

SEQUENCE LISTING

<160> NUMBER OF SEQ ID NOS: 10

<210> SEQ ID NO 1
<211> LENGTH: 1675
<212> TYPE: DNA
<213> ORGANISM: Pseudomonas sp.

<400> SEQUENCE: 1

```
tttttcgatg gcataatatc tgcgttgcga cgtgtaacac actattggag acatatcatg      60
caaacgctca gcatccagca cggtaccctc gtcacgatgg atcagtaccg cagagtcctt     120
ggggatagct gggttcacgt gcaggatgga cggatcgtcg cgctcggagt gcacgccgag     180
tcggtgcctc cgccagcgga tcgggtgatc gatgcacgcg gcaaggtcgt gttacccggt     240
ttcatcaatg cccacaccca tgtgaaccag atcctcctgc gcggagggcc ctcgcacggg     300
cgtcaattct atgactggct gttcaacgtt gtgtatccgg acaaaaggc gatgagaccg      360
gaggacgtag cggtggcggt gaggttgtat tgtgcgaag ctgtgcgcag cgggattacg      420
acgatcaacg aaaacgccga ttcggccatc tacccaggca acatcgaggc cgcgatggcg     480
gtctatggtg aggtgggtgt gagggtcgtc tacgcccgca tgttctttga tcggatggac     540
gggcgcattc aagggtatgt ggacgccttg aaggctcgct ctccccaagt cgaactgtgc     600
tcgatcatgg aggaaacggc tgtggccaaa gatcggatca cagccctgtc agatcagtat     660
catggcacgg caggaggtcg tatatcagtt tggcccgctc ctgccactac cacggcggtg     720
acagttgaag gaatgcgatg ggcacaagcc ttcgcccgtg atcgggcggt aatgtggacg     780
cttcacatgg cggagagcga tcatgatgag cggattcatg ggatgagtcc cgccgagtac     840
atggagtgtt acggactctt ggatgagcgt ctgcaggtcg cgcattgcgt gtactttgac     900
cggaaggatg ttcggctgct gcaccgccac aatgtgaagg tcgcgtcgca ggttgtgagc     960
aatgcctacc tcggctcagg ggtggccccc gtgccagaga tggtggagcg cggcatggcc    1020
gtgggcattg aacagataa cgggaatagt aatgactccg taaacatgat cggagacatg     1080
aagtttatgg cccatattca ccgcgcggtg catcgggatg cggacgtgct gaccccagag    1140
aagattcttg aaatggcgac gatcgatggg gcgcgttcgt tgggaatgga ccacgagatt    1200
ggttccatcg aaaccggcaa gcgcgcggac cttatcctgc ttgacctgcg tcaccctcag    1260
acgactcctc accatcattt ggcggccacg atcgtgtttc aggcttacgg caatgaggtg    1320
gacactgtcc tgattgacgg aaacgttgtg atggagaacc gccgcttgag ctttcttccc    1380
cctgaacgtg agttggcgtt ccttgaggaa gcgcagagcc gcgccacagc tattttgcag    1440
cgggcgaaca tggtggctaa cccagcttgg cgcagcctct aggaaatgac gccgttgctg    1500
catccgccgc cccttgagga aatcgctgcc atcttggcgc ggctcggatt gggggggcgga    1560
catgaccttg atggatacag aattgccatg aatgcggcac ttccgtcctt cgctcgtgtg    1620
gaatcgttgg taggtgaggg tcgactgcgg gcgccagctt cccgaagagg tgaaa        1675
```

<210> SEQ ID NO 2
<211> LENGTH: 474
<212> TYPE: PRT
<213> ORGANISM: Pseudomonas sp.

<400> SEQUENCE: 2

```
Met Gln Thr Leu Ser Ile Gln His Gly Thr Leu Val Thr Met Asp Gln
 1               5                  10                  15
```

-continued

```
Tyr Arg Arg Val Leu Gly Asp Ser Trp Val His Val Gln Asp Gly Arg
             20                  25                  30

Ile Val Ala Leu Gly Val His Ala Glu Ser Val Pro Pro Pro Ala Asp
         35                  40                  45

Arg Val Ile Asp Ala Arg Gly Lys Val Val Leu Pro Gly Phe Ile Asn
     50                  55                  60

Ala His Thr His Val Asn Gln Ile Leu Arg Gly Gly Pro Ser His
 65                  70                  75                  80

Gly Arg Gln Phe Tyr Asp Trp Leu Phe Asn Val Val Tyr Pro Gly Gln
                 85                  90                  95

Lys Ala Met Arg Pro Glu Asp Val Ala Val Ala Val Arg Leu Tyr Cys
                100                 105                 110

Ala Glu Ala Val Arg Ser Gly Ile Thr Thr Ile Asn Glu Asn Ala Asp
            115                 120                 125

Ser Ala Ile Tyr Pro Gly Asn Ile Glu Ala Ala Met Ala Val Tyr Gly
        130                 135                 140

Glu Val Gly Val Arg Val Val Tyr Ala Arg Met Phe Phe Asp Arg Met
145                 150                 155                 160

Asp Gly Arg Ile Gln Gly Tyr Val Asp Ala Leu Lys Ala Arg Ser Pro
                165                 170                 175

Gln Val Glu Leu Cys Ser Ile Met Glu Glu Thr Ala Val Ala Lys Asp
            180                 185                 190

Arg Ile Thr Ala Leu Ser Asp Gln Tyr His Gly Thr Ala Gly Gly Arg
        195                 200                 205

Ile Ser Val Trp Pro Ala Pro Ala Thr Thr Thr Ala Val Thr Val Glu
    210                 215                 220

Gly Met Arg Trp Ala Gln Ala Phe Ala Arg Asp Arg Ala Val Met Trp
225                 230                 235                 240

Thr Leu His Met Ala Glu Ser Asp His Asp Glu Arg Ile His Gly Met
                245                 250                 255

Ser Pro Ala Glu Tyr Met Glu Cys Tyr Gly Leu Leu Asp Glu Arg Leu
            260                 265                 270

Gln Val Ala His Cys Val Tyr Phe Asp Arg Lys Asp Val Arg Leu Leu
        275                 280                 285

His Arg His Asn Val Lys Val Ala Ser Gln Val Val Ser Asn Ala Tyr
    290                 295                 300

Leu Gly Ser Gly Val Ala Pro Val Pro Glu Met Val Glu Arg Gly Met
305                 310                 315                 320

Ala Val Gly Ile Gly Thr Asp Asn Gly Asn Ser Asn Asp Ser Val Asn
                325                 330                 335

Met Ile Gly Asp Met Lys Phe Met Ala His Ile His Arg Ala Val His
            340                 345                 350

Arg Asp Ala Asp Val Leu Thr Pro Glu Lys Ile Leu Glu Met Ala Thr
        355                 360                 365

Ile Asp Gly Ala Arg Ser Leu Gly Met Asp His Glu Ile Gly Ser Ile
    370                 375                 380

Glu Thr Gly Lys Arg Ala Asp Leu Ile Leu Leu Asp Leu Arg His Pro
385                 390                 395                 400

Gln Thr Thr Pro His His His Leu Ala Ala Thr Ile Val Phe Gln Ala
                405                 410                 415

Tyr Gly Asn Glu Val Asp Thr Val Leu Ile Asp Gly Asn Val Val Met
            420                 425                 430

Glu Asn Arg Arg Leu Ser Phe Leu Pro Pro Glu Arg Glu Leu Ala Phe
```

```
                435                 440                 445
Leu Glu Glu Ala Gln Ser Arg Ala Thr Ala Ile Leu Gln Arg Ala Asn
    450                 455                 460

Met Val Ala Asn Pro Ala Trp Arg Ser Leu
465                 470
```

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 3
ggctgtctat ggtgaggtg                                           19

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 4
ccgaggtagg cattgctca                                           19

<210> SEQ ID NO 5
<211> LENGTH: 59
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 5
attgacgtcc gtgtgaggga cctccgcgca ggaggatctg gttcacatgg gtgtgggca    59

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 6
ccatgtgaac cagatcct                                            18

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 7
tgaagcgtcc acattacc                                            18

<210> SEQ ID NO 8
<211> LENGTH: 1495
<212> TYPE: DNA
<213> ORGANISM: Artificial Sequence
<220> FEATURE:

<223> OTHER INFORMATION: Description of Artificial Sequence: An atzA
      coding region modified to contain codons to optimize
      expression in plants

<400> SEQUENCE: 8

```
tgctctagaa gttttatttt ttaatttct ttcaaatact tccatctgga gacaacaatg      60
gaaactctca gcatccagca cggtaccctc gtcactatgg atcagtaccg cagagtcctt    120
ggtgatagct gggttcacgt gcaggatgga cgtatcgtcg ctctcggagt gcacgccgag    180
tcagtgcctc ctccagctga tcgtgtgatc gatgcacgcg gcaaggtcgt gttacccggt    240
ttcatcaatg cccacaccca tgtgaaccag atcctcctgc gcggaggtcc ctcacacgga    300
cgtcaattct atgactggct gttcaacgtt gtgtatcctg acaaaaggc tatgagacct    360
gaggacgtag ctgtggcagt gaggttgtat tgtgctgaag ctgtgcgcag cggtattact    420
actatcaacg aaaacgccga ttctgccatc tacccaggca acatcgaggc cgctatggct    480
gtctatggtg aagtgggtgt gagggtcgtc tacgcccgca tgttctttga tcgtatggac    540
ggacgcattc aaggttatgt ggacgccttg aaggctcgct ctccccaagt cgaactgtgc    600
tcaatcatgg aggaaactgc tgtggccaaa gatcgtatca cagccctgtc agatcagtat    660
catggcactg caggaggtcg tatatcagtt tggcccgctc ctgccactac cactgcagtg    720
acagttgaag gaatgcgatg gcacaagcc ttcgcccgtg atcgtgctgt tatgtggact    780
cttcacatgg ctgagagcga tcatgatgag cgtattcatg gtatgagtcc cgccgagtac    840
atggagtgtt acggactctt ggatgagcgt ctgcaggtcg ctcattgcgt gtactttgac    900
cgtaaggatg ttcgactgct gcaccgccac aatgtgaagg tcgcgtcaca ggttgtgagc    960
aatgcctacc tcggctcagg tgtggccccc gtgccagaga tggtggagcg cggcatggcc   1020
gtgggcattg aacagataa cggcaatagt aatgactccg taaacatgat cggagacatg   1080
aagtttatgg cccatattca ccgcgctgtg catcgtgatg ctgacgtgct gaccccagag   1140
aagattcttg aaatggctac aatcgatggt gctcgttcat tgggaatgga ccacgagatt   1200
ggttccatcg aaaccggcaa gcgcgctgac cttatcctgc ttgacctgcg tcaccctcag   1260
acgactcctc accatcattt ggctgccaca atcgtgtttc aggcttacgg caatgaggtg   1320
gacactgtcc tgattgacgg aaacgttgtg atggagaacc gccgcttgag ctttcttccc   1380
cctgaacgtg agttggcatt ccttgaggaa gctcagagcc gcgccacagc tattttgcag   1440
cgtgctaaca tggtggctaa cccagcttgg cgcagcctct aaaagagctc acgcc        1495
```

<210> SEQ ID NO 9
<211> LENGTH: 474
<212> TYPE: PRT
<213> ORGANISM: Artificial Sequence
<220> FEATURE:
<223> OTHER INFORMATION: Description of Artificial Sequence: The protein
      encoded by SEQ ID NO:8

<400> SEQUENCE: 9

```
Met Glu Thr Leu Ser Ile Gln His Gly Thr Leu Val Thr Met Asp Gln
  1               5                  10                  15

Tyr Arg Arg Val Leu Gly Asp Ser Trp Val His Val Gln Asp Gly Arg
                 20                  25                  30

Ile Val Ala Leu Gly Val His Ala Glu Ser Val Pro Pro Ala Asp
             35                  40                  45

Arg Val Ile Asp Ala Arg Gly Lys Val Val Leu Pro Gly Phe Ile Asn
         50                  55                  60
```

-continued

```
Ala His Thr His Val Asn Gln Ile Leu Leu Arg Gly Pro Ser His
 65                  70                  75                  80

Gly Arg Gln Phe Tyr Asp Trp Leu Phe Asn Val Val Tyr Pro Gly Gln
                 85                  90                  95

Lys Ala Met Arg Pro Glu Asp Val Ala Val Ala Val Arg Leu Tyr Cys
                100                 105                 110

Ala Glu Ala Val Arg Ser Gly Ile Thr Thr Ile Asn Glu Asn Ala Asp
                115                 120                 125

Ser Ala Ile Tyr Pro Gly Asn Ile Glu Ala Ala Met Ala Val Tyr Gly
            130                 135                 140

Glu Val Gly Val Arg Val Val Tyr Ala Arg Met Phe Phe Asp Arg Met
145                 150                 155                 160

Asp Gly Arg Ile Gln Gly Tyr Val Asp Ala Leu Lys Ala Arg Ser Pro
                165                 170                 175

Gln Val Glu Leu Cys Ser Ile Met Glu Glu Thr Ala Val Ala Lys Asp
                180                 185                 190

Arg Ile Thr Ala Leu Ser Asp Gln Tyr His Gly Thr Ala Gly Gly Arg
            195                 200                 205

Ile Ser Val Trp Pro Ala Pro Ala Thr Thr Thr Ala Val Thr Val Glu
            210                 215                 220

Gly Met Arg Trp Ala Gln Ala Phe Ala Arg Asp Arg Ala Val Met Trp
225                 230                 235                 240

Thr Leu His Met Ala Glu Ser Asp His Asp Glu Arg Ile His Gly Met
                245                 250                 255

Ser Pro Ala Glu Tyr Met Glu Cys Tyr Gly Leu Leu Asp Glu Arg Leu
                260                 265                 270

Gln Val Ala His Cys Val Tyr Phe Asp Arg Lys Asp Val Arg Leu Leu
            275                 280                 285

His Arg His Asn Val Lys Val Ala Ser Gln Val Val Ser Asn Ala Tyr
            290                 295                 300

Leu Gly Ser Gly Val Ala Pro Val Pro Glu Met Val Glu Arg Gly Met
305                 310                 315                 320

Ala Val Gly Ile Gly Thr Asp Asn Gly Asn Ser Asn Asp Ser Val Asn
                325                 330                 335

Met Ile Gly Asp Met Lys Phe Met Ala His Ile His Arg Ala Val His
            340                 345                 350

Arg Asp Ala Asp Val Leu Thr Pro Glu Lys Ile Leu Glu Met Ala Thr
            355                 360                 365

Ile Asp Gly Ala Arg Ser Leu Gly Met Asp His Glu Ile Gly Ser Ile
            370                 375                 380

Glu Thr Gly Lys Arg Ala Asp Leu Ile Leu Leu Asp Leu Arg His Pro
385                 390                 395                 400

Gln Thr Thr Pro His His His Leu Ala Ala Thr Ile Val Phe Gln Ala
                405                 410                 415

Tyr Gly Asn Glu Val Asp Thr Val Leu Ile Asp Gly Asn Val Val Met
                420                 425                 430

Glu Asn Arg Arg Leu Ser Phe Leu Pro Pro Glu Arg Glu Leu Ala Phe
            435                 440                 445

Leu Glu Glu Ala Gln Ser Arg Ala Thr Ala Ile Leu Gln Arg Ala Asn
            450                 455                 460

Met Val Ala Asn Pro Ala Trp Arg Ser Leu
465                 470
```

```
<210> SEQ ID NO 10
<211> LENGTH: 53
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 10
accccagaga agattcttga aatggctaca atcgatggtg ctcgttcatt ggg          53
```